(12) United States Patent
Strano et al.

(10) Patent No.: US 12,105,024 B2
(45) Date of Patent: Oct. 1, 2024

(54) SUBSTRATE-IMMOBILIZED OPTICAL NANOSENSORS

(71) Applicant: MASSACHUSETTS INSTITUTE OF TECHNOLOGY, Cambridge, MA (US)

(72) Inventors: Michael Strano, Lexington, MA (US); Xun Gong, Cambridge, MA (US); Daniel Salem, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 458 days.

(21) Appl. No.: 17/291,110

(22) PCT Filed: Nov. 6, 2019

(86) PCT No.: PCT/US2019/060159
§ 371 (c)(1),
(2) Date: May 4, 2021

(87) PCT Pub. No.: WO2020/097268
PCT Pub. Date: May 14, 2020

(65) Prior Publication Data
US 2022/0003682 A1    Jan. 6, 2022

Related U.S. Application Data

(60) Provisional application No. 62/757,108, filed on Nov. 7, 2018, provisional application No. 62/803,440, filed on Feb. 9, 2019.

(51) Int. Cl.
*G01N 21/77* (2006.01)
*G01N 33/543* (2006.01)

(52) U.S. Cl.
CPC ....... *G01N 21/77* (2013.01); *G01N 33/54346* (2013.01); *G01N 2021/7759* (2013.01);
(Continued)

(58) Field of Classification Search
CPC ............... G01N 21/77; G01N 33/5436; G01N 2021/7759; G01N 2021/7796; G01N 2021/7786
See application file for complete search history.

(56) References Cited

U.S. PATENT DOCUMENTS 6,471,745 B1 * 10/2002 Foley .................. B01D 71/021
                                                    502/182
6,719,147 B2 * 4/2004 Strano ................. B01D 67/003
                                                    210/500.22

(Continued)

FOREIGN PATENT DOCUMENTS

CN         104807987 A      7/2015

OTHER PUBLICATIONS

Bardecker et al., Directed Assembly of Single-Walled Carbon Nanotubes via Drop-Casting onto a UV-Patterned Photosensitive Monolayer, J. Am. Chem. Soc. 2008, 130, 7226-7227 (Year: 2008).*

(Continued)

*Primary Examiner* — Peter Radkowski
(74) *Attorney, Agent, or Firm* — Honigman LLP

(57) ABSTRACT

A sensor for detecting an analyte can include a photoluminescent nanostructure embedded in a sensor porous planar substrate. The sensor porous planar substrate can be supported by a substrate porous planar substrate.

17 Claims, 43 Drawing Sheets

(52) U.S. Cl.
CPC ............... *G01N 2021/7786* (2013.01); *G01N 2021/7796* (2013.01)

(56) References Cited

U.S. PATENT DOCUMENTS

| | | | | |
|---|---|---|---|---|
| 7,572,426 | B2* | 8/2009 | Strano | C01B 32/174 |
| | | | | 977/734 |
| 7,887,774 | B2* | 2/2011 | Strano | C09C 1/48 |
| | | | | 423/447.2 |
| 7,955,559 | B2* | 6/2011 | Joshi | B82Y 15/00 |
| | | | | 977/723 |
| 8,058,628 | B2* | 11/2011 | Zywno | B82Y 10/00 |
| | | | | 250/442.11 |
| 8,377,700 | B2* | 2/2013 | Strano | B82Y 15/00 |
| | | | | 435/7.1 |
| 8,460,608 | B2* | 6/2013 | Strano | G01N 21/643 |
| | | | | 422/82.07 |
| 8,486,709 | B2* | 7/2013 | Strano | G01N 33/54373 |
| | | | | 977/788 |
| 8,765,488 | B2* | 7/2014 | Strano | B82Y 15/00 |
| | | | | 435/14 |
| 8,941,285 | B2* | 1/2015 | Strano | B82Y 10/00 |
| | | | | 427/538 |
| 9,403,684 | B2* | 8/2016 | Strano | B82Y 40/00 |
| 9,588,077 | B2* | 3/2017 | Joshi | A61B 5/14865 |
| 9,664,677 | B2* | 5/2017 | Strano | G01N 33/542 |
| 10,012,657 | B2* | 7/2018 | Strano | G01N 33/54346 |
| 10,338,051 | B2* | 7/2019 | Strano | G01N 21/643 |
| 10,712,347 | B2* | 7/2020 | Strano | B82Y 15/00 |
| 2003/0034295 | A1* | 2/2003 | Strano | B01D 71/021 |
| | | | | 210/488 |
| 2007/0292896 | A1* | 12/2007 | Strano | G01N 33/551 |
| | | | | 435/7.9 |
| 2008/0063587 | A1* | 3/2008 | Strano | C09C 1/56 |
| | | | | 204/450 |
| 2009/0028683 | A1* | 1/2009 | Zywno | H01J 37/3174 |
| | | | | 414/754 |
| 2009/0084678 | A1* | 4/2009 | Joshi | A61B 5/14865 |
| | | | | 204/403.14 |
| 2010/0028247 | A1* | 2/2010 | Strano | C09C 1/48 |
| | | | | 423/447.2 |
| 2010/0179068 | A1* | 7/2010 | Kaiser | B01L 3/50273 |
| | | | | 506/9 |
| 2010/0279421 | A1* | 11/2010 | Strano | B82Y 15/00 |
| | | | | 436/95 |
| 2011/0045523 | A1* | 2/2011 | Strano | G01N 33/54346 |
| | | | | 436/151 |
| 2011/0204258 | A1* | 8/2011 | Heller | B82Y 15/00 |
| | | | | 977/750 |
| 2011/0240344 | A1* | 10/2011 | Strano | H10K 71/12 |
| | | | | 428/209 |
| 2011/0257033 | A1* | 10/2011 | Strano | G01N 33/542 |
| | | | | 435/7.1 |
| 2011/0269243 | A1* | 11/2011 | Strano | B82Y 30/00 |
| | | | | 977/750 |
| 2011/0280912 | A1* | 11/2011 | Langer | B82Y 30/00 |
| | | | | 524/602 |
| 2012/0018301 | A1* | 1/2012 | Joshi | A61B 5/14865 |
| | | | | 977/890 |
| 2012/0178640 | A1* | 7/2012 | Strano | B82Y 5/00 |
| | | | | 506/13 |
| 2012/0262027 | A1* | 10/2012 | Strano | B82Y 10/00 |
| | | | | 310/306 |
| 2013/0035567 | A1* | 2/2013 | Strano | G01N 33/54373 |
| | | | | 977/750 |
| 2013/0230464 | A1* | 9/2013 | Yi | A61K 49/0058 |
| | | | | 435/7.37 |
| 2013/0260396 | A1* | 10/2013 | Akcakir | G01N 33/5029 |
| | | | | 435/7.25 |
| 2014/0080122 | A1* | 3/2014 | Strano | G01N 33/54373 |
| | | | | 536/26.6 |
| 2014/0199229 | A1* | 7/2014 | Strano | B82Y 40/00 |
| | | | | 423/447.2 |
| 2014/0234856 | A1* | 8/2014 | Reuel | G01N 33/5436 |
| | | | | 435/7.1 |
| 2014/0308681 | A1* | 10/2014 | Strano | B82Y 15/00 |
| | | | | 435/7.8 |
| 2014/0353154 | A1* | 12/2014 | Joshi | B82Y 15/00 |
| | | | | 205/792 |
| 2015/0047074 | A1* | 2/2015 | Strano | A01H 3/00 |
| | | | | 435/317.1 |
| 2015/0050208 | A1* | 2/2015 | Carlson | C01B 32/174 |
| | | | | 423/447.2 |
| 2015/0133752 | A1* | 5/2015 | Iverson | A61B 5/1459 |
| | | | | 600/316 |
| 2016/0178597 | A1* | 6/2016 | Strano | G01N 21/6428 |
| | | | | 436/501 |
| 2017/0131287 | A1* | 5/2017 | McNicholas | G01N 33/582 |
| 2017/0299601 | A1* | 10/2017 | Giraldo Gomez | B82Y 15/00 |
| 2017/0328890 | A1* | 11/2017 | Strano | B82Y 30/00 |
| 2018/0011072 | A1* | 1/2018 | Strano | G01N 21/6489 |

OTHER PUBLICATIONS

Carrilho et al., Understanding Wax Printing: A Simple Micropatterning Process for Paper-Based Microfluidics, Anal. Chem. 2009, 81 , 16, 7091-7095, Jul. 15, 2009, https://doi.org/10.1021/ac901071p (Year: 2009).*

Davis et al., Creating Controlled Thickness Gradients in Polymer Thin Films via Flowcoating, Langmuir 2014, 30, 5637-5644, dx.doi.org/10.1021/la501247x (Year: 2014).*

Heller et al., Peptide secondary structure modulates single-walled carbon nanotube fluorescence as a chaperone sensor for nitroaromatics, Proceedings of the National Academy of Sciences, May 9, 2011, 108 (21) 8544-8549, https://doi.org/10.1073/pnas.1005512108 (Year: 2011).*

Ellerbee et al., Quantifying Colorimetric Assays in Paper-Based Microfluidic Devices by Measuring the Transmission of Light through Paper, Analytical Chemistry 2009, 81, 20, 8447-842, DOI: 10.1021/ac901307q (Year: 2009).*

Glavan et al., Analytical Devices Based on Direct Synthesis of DNA on Paper, Analytical Chemistry 2016, 88, 1, 725-731, DOI: 10.1021/acs.analchem.5b02822 (Year: 2016).*

Zhang, J., Landry, M., Barone, P. et al. Molecular recognition using corona phase complexes made of synthetic polymers adsorbed on carbon nanotubes. Nature Nanotech 8, 959-968 (2013). https://doi.org/10.1038/nnano.2013.236 (Year: 2013).*

Han, Jin-Woo & Kim, Beomseok & Li, Jing & Meyyappan, M.. (2014). Carbon nanotube ink for writing on cellulose paper. Materials Research Bulletin. 50. 249-253. 10.1016/j.materresbull.2013.10.048. (Year: 2014).*

Kaplan et al., Excitation intensity dependence of photoluminescence from monolayers of MoS2 and WS2 /MoS2 heterostructures, 2016 2D Mater. 3 015005 (Year: 2016).*

Han et al., Carbon Nanotube Based Humidity Sensor on Cellulose Paper, J. Phys. Chem. C 116 (2012) 22094. (Year: 2012).*

International Search Report issued on Jan. 30, 2020 in corresponding International Patent Application No. PCT/US2019/060159.

Written Opinion of the International Searching Authority issued on Jan. 30, 2020 in corresponding International Patent Application No. PCT/US2019/060159.

* cited by examiner

Deployment of SWNT sensors requires some form of sensor immobilization

Solution phase deployment

- Sensors are dispersed in solution with analyte
- Currently limited to water-based systems
- Resulting SWNT solution must be treated as hazardous waste

Hydrogel encapsulation

- Sensors are immobilized within a porous hydrogel network
- Currently limited to water-based systems
- Unclear how sensor performance is affected by drying, microbial contamination, etc.

Surface immobilization

- Sensors are immobilized on a functionalized glass or plastic surface
- Strength of surface immobilization sensitive to analyte solution properties (e.g., pH)
- Functionalized substrates may be costly (>$5 for slide)

Paper immobilization

- Has not yet been reported for SWNT optical sensors
- Sensors are immobilized within a paper/membrane fibrous network and stored dry
- Compatible with water-based and oil-based systems

Figure 9

Advantages of paper form factor

Inexpensive substrate for sensor immobilization
- < $0.03 per $cm^2$ from Sigma Aldrich Ease of storage and transport
- Can be stored dry at various temperatures and humidities Already implemented in medical diagnostics and other routine chemical tests

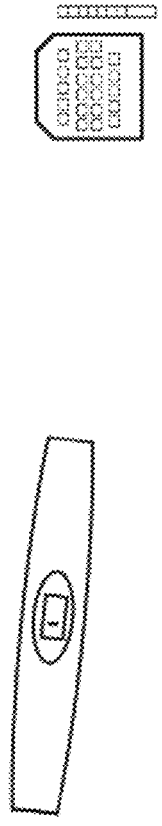

Can interface with existing laboratory instrumentation for collecting sensor measurements

Figure 10

Metal ion response data measured from sensor barcodes

Sensor name (ssDNA wrapping) →

| | (TCA)6 | (TCC)6 | (TCG)6 | C30 | (CCG)4 | (TAT)4 | (ATT)3 | (GT)15 |
|---|---|---|---|---|---|---|---|---|
| Cu | -0.45 | -0.55 | -0.46 | -0.13 | -0.46 | -0.58 | -0.54 | 1.13 |
| | -0.46 | -0.47 | -0.69 | -0.30 | -0.52 | -0.54 | -0.41 | 1.35 |
| | -0.59 | -0.56 | -0.67 | -0.22 | -0.56 | -0.63 | -0.43 | 2.63 |
| | -0.21 | -0.08 | -0.01 | -0.23 | -0.43 | -0.18 | -0.16 | 0.54 |
| | -0.52 | -0.58 | -0.56 | -0.31 | -0.53 | -0.45 | -0.41 | 2.29 |
| | -0.40 | -0.37 | -0.55 | -0.27 | -0.50 | -0.54 | -0.37 | 1.08 |
| | -0.50 | -0.59 | -0.69 | -0.26 | -0.53 | -0.49 | 0.07 | 1.02 |
| | -0.23 | -0.08 | -0.38 | -0.25 | -0.47 | -0.20 | -0.14 | 0.98 |
| Hg | -0.09 | -0.29 | 0.66 | -0.55 | 1.11 | -0.36 | 0.56 | 0.09 |
| | 0.05 | -0.13 | 0.20 | -0.43 | 0.53 | -0.35 | 0.41 | -0.43 |
| | -0.09 | -0.34 | -0.14 | -0.42 | 0.77 | -0.23 | -0.14 | -0.20 |
| | -0.11 | -0.29 | -0.14 | -0.38 | 0.30 | 0.10 | 0.74 | 1.35 |
| | -0.10 | 0.19 | 0.24 | -0.40 | 1.77 | -0.36 | 0.35 | -0.27 |
| | -0.03 | -0.14 | -0.20 | -0.48 | 0.42 | -0.31 | 0.54 | -0.14 |
| | -0.26 | -0.38 | 0.14 | -0.41 | 0.63 | -0.36 | -0.06 | -0.42 |
| | -0.05 | -0.36 | -0.19 | -0.34 | 0.37 | 0.18 | 0.90 | 1.66 |
| Pb | -0.31 | -0.71 | -0.75 | -0.22 | -0.72 | -0.41 | -0.22 | -0.32 |
| | -0.48 | -0.81 | -0.83 | -0.32 | -0.81 | -0.37 | -0.08 | -0.29 |
| | -0.31 | -0.72 | -0.77 | -0.23 | -0.72 | -0.15 | -0.32 | -0.45 |
| | -0.45 | -0.70 | -0.79 | -0.21 | -0.69 | -0.47 | -0.37 | -0.44 |
| | -0.43 | -0.74 | -0.85 | -0.27 | -0.72 | -0.26 | 0.24 | -0.07 |
| | -0.52 | -0.74 | -0.86 | -0.28 | -0.83 | -0.31 | -0.28 | -0.38 |
| | -0.43 | -0.75 | -0.87 | -0.27 | -0.72 | | | |
| | -0.44 | -0.72 | -0.79 | -0.27 | -0.68 | | | |
| Cd | -0.35 | -0.36 | -0.58 | -0.10 | -0.41 | -0.22 | -0.12 | -0.16 |
| | -0.10 | -0.20 | -0.63 | -0.07 | -0.39 | -0.24 | -0.14 | 0.21 |
| | -0.25 | -0.09 | -0.43 | 0.34 | -0.31 | -0.19 | 0.04 | 0.20 |
| | -0.24 | 0.08 | 0.04 | -0.09 | -0.32 | -0.32 | -0.12 | -0.21 |
| | -0.21 | -0.32 | -0.54 | -0.10 | -0.39 | -0.23 | -0.03 | 0.20 |
| | -0.28 | -0.30 | -0.57 | -0.19 | -0.47 | -0.13 | -0.01 | 0.36 |
| | -0.30 | -0.33 | -0.72 | -0.20 | -0.33 | | | |
| | -0.17 | 0.07 | -0.29 | 0.10 | -0.39 | | | |
| | -0.26 | 0.19 | -0.05 | -0.01 | -0.20 | | | |
| | -0.30 | -0.30 | -0.54 | -0.07 | -0.30 | | | |

Figure 19

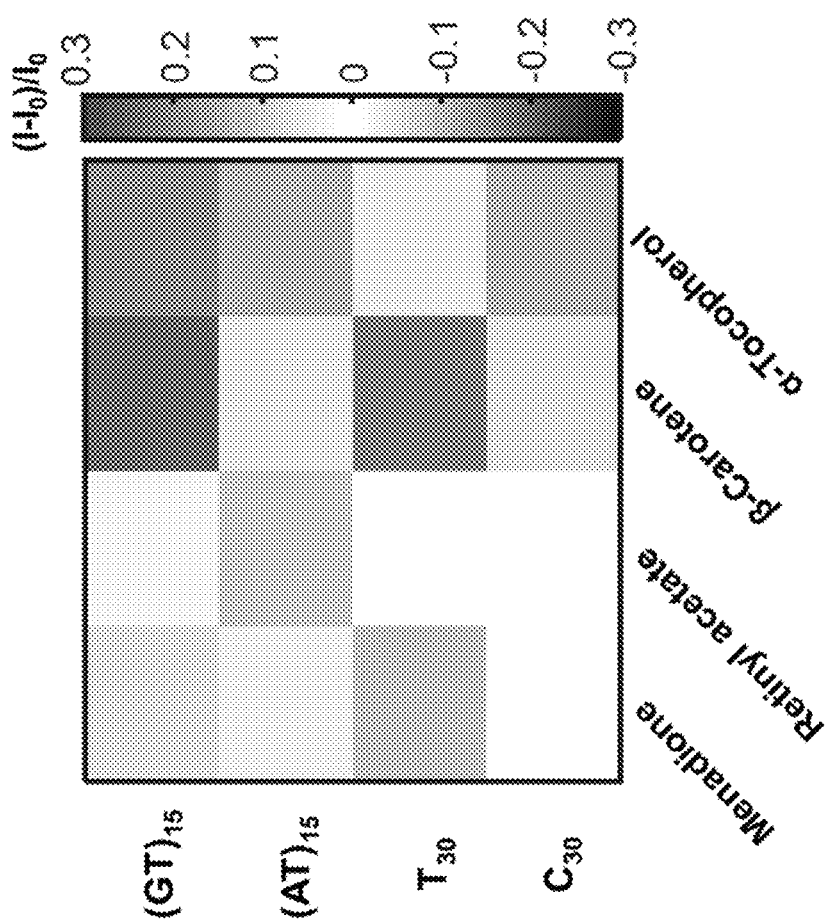
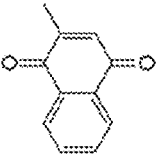
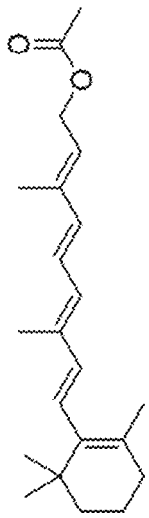
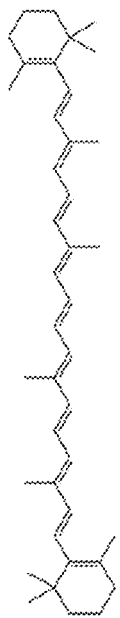
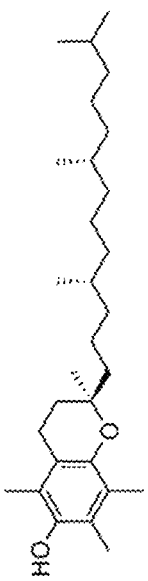
Figure 27

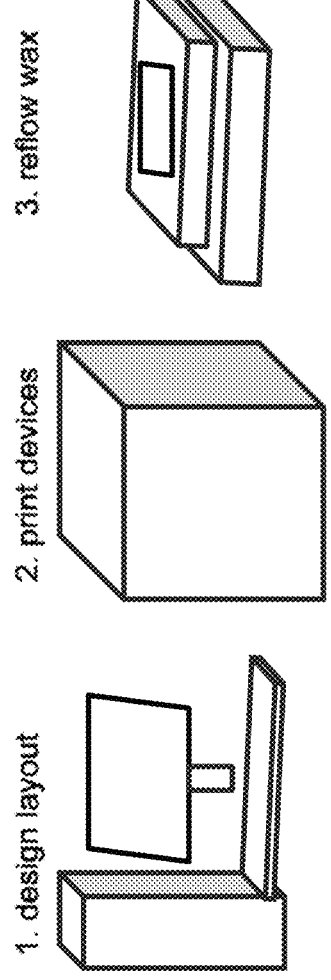
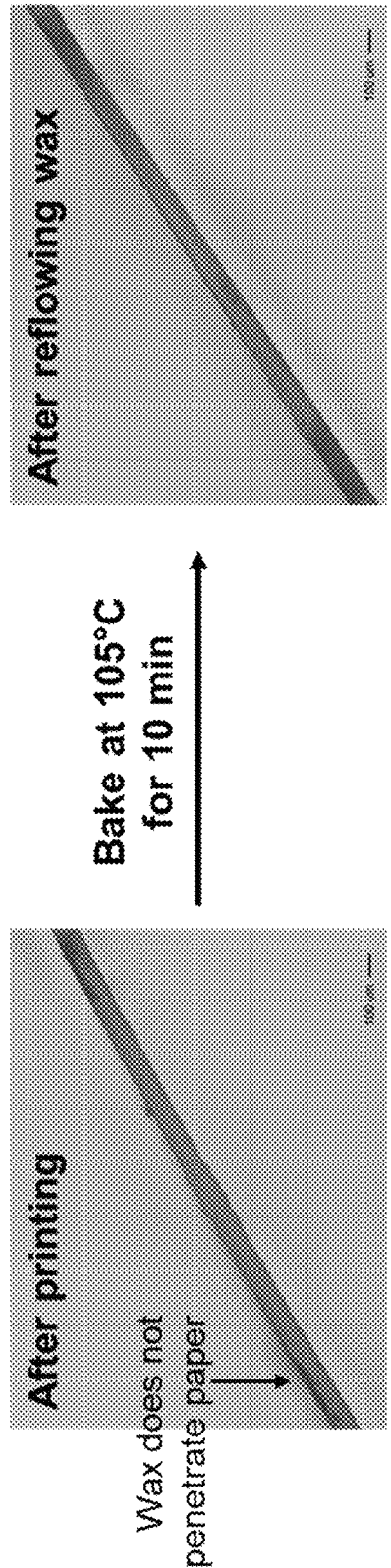
Figure 29

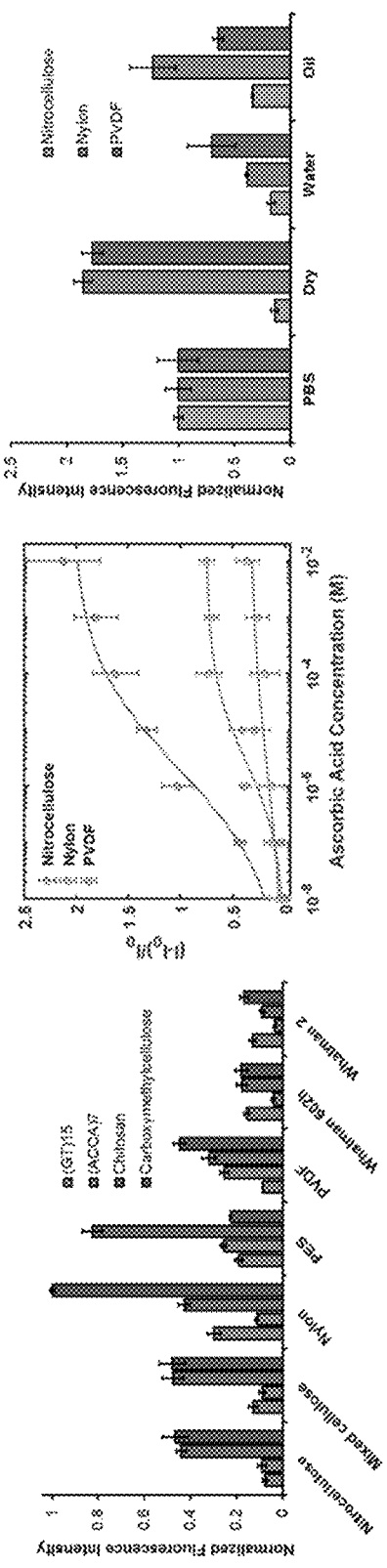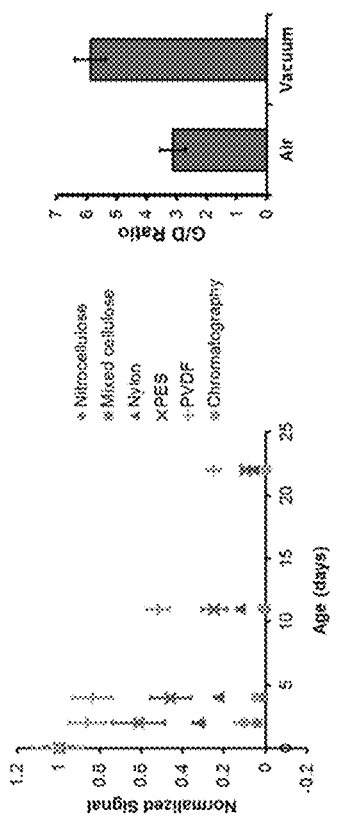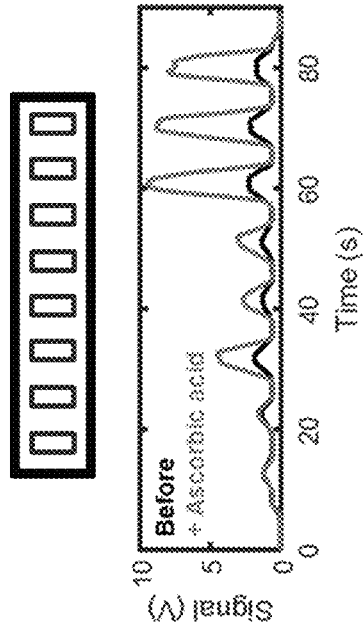
Figure 35

SUBSTRATE-IMMOBILIZED OPTICAL NANOSENSORS

PRIORITY CLAIM

This application is a National Phase application filed under 35 USC § 371 of International Application No. PCT/US2019/060159, filed on Nov. 6, 2019, which claims the benefit of prior filed U.S. Provisional Patent Application No. 62/757,108, filed Nov. 7, 2018 and U.S. Provisional Patent Application No. 62/803,440, filed Feb. 9, 2019, each of which is incorporated by reference in its entirety.

TECHNICAL FIELD

The present invention relates to a substrate-immobilized optical nanosensors.

BACKGROUND

On-line analytical technology for the production recombinant proteins is an area of great interest. Product titer and post-translational modifications are important process parameters to be monitored. Some post-translational modifications, such as glycosylation patterns, can change in response to changes in process conditions (e.g., media components, temperature, pH, $pCO_2$, dissolved oxygen, cell density, duration, and others) and can have a dramatic effect on the properties of the protein product (e.g., pharmacokinetics and immunogenicity of a protein drug). Current analytical technologies for determining titer and glycosylation, such as ELISA and tandem LC/MS systems, respectively, can deliver detailed information but are costly in terms of time, reagents, and multiplexing capabilities. Furthermore, these methods are incompatible with on-line process use.

SUMMARY

In general, a sensor can include a porous planar substrate and at least one photoluminescent nanostructure on or embedded within the porous planar substrate.

In another aspect, a method of detecting an analyte can include contacting a composition including an analyte to a sensor including: a porous planar substrate and a photoluminescent nanostructure on the porous planar substrate.

In some embodiments, the method of detecting the analyte can further include detecting photoluminescence from the photoluminescent nanostructure.

In another aspect, a sensor for detecting one or more analytes can include a porous planar substrate, and at least one photoluminescent nanostructure on or embedded within the sensor porous planar substrate.

In certain circumstances, the sensor can include an analyte-binding compound associated with the photoluminescent nanostructure.

In certain circumstances, the photoluminescent nanostructure can include a polymer. The polymer can include a polypeptide, a polynucleotide or a polysaccharide. In certain circumstances, the polymer can be a polynucleotide.

In certain circumstances, the sensor can include a plurality of regions on the porous planar substrate, at least one of the plurality of regions includes a first region including the at least one photoluminescent nanostructure. The plurality of regions can include a second region including at least one photoluminescent nanostructure different from the at least one photoluminescent nanostructure.

In certain circumstances, the sensor can include a plurality of regions including two, three, four, five, six, seven, eight, nine, ten, eleven, twelve or more distinct regions. Each distinct region can include a different photoluminescent nanostructure or composition.

In certain circumstances, the porous planar substrate can include a paper, nitrocellulose, or nylon, or combinations thereof.

In another aspect, a method of making a sensor for detecting one or more analytes can include depositing a photoluminescent nanostructure on or within a porous planar substrate.

In certain circumstances, the method can include patterning the porous planar substrate to include a plurality of regions, at least one region receiving the photoluminescent nanostructure.

In certain circumstances, the method can include depositing includes placing a liquid including the photoluminescent nanostructure on the porous planar substrate.

In another aspect, a method of detecting an analyte can include contacting a sensor including a photoluminescent nanostructure on or embedded within the porous planar substrate with a sample; and detecting an output from the sample to determine the presence of the analyte.

In certain circumstances, the method can include measuring the output at two or more regions of the porous planar substrate.

In certain circumstances, the method can include moving the porous planar substrate relative to a detector.

In certain circumstances, the method can include moving the porous planar substrate relative to a detector at a controlled rate.

In another aspect, a system for detecting an analyte can include a platform including a sample holder, a detector including a directed at the platform, and a translation stage including an axis of motion orthogonal to the contacting a sensor including a photoluminescent nanostructure on or embedded within the porous planar substrate with a sample.

In certain circumstances, the system can include a translation stage moves the platform at a controlled rate.

In certain circumstances, the system can include an photoexcitation device.

Other aspects, embodiments, and features will be apparent from the following description, the drawings, and the claims.

BRIEF DESCRIPTION OF THE DRAWINGS

FIGS. 9-35 depict sensors, systems and methods described herein.

DETAILED DESCRIPTION

Sensors including porous planar substrates and photoluminescent nanostructures are described, as well as systems and methods using the sensors. The photoluminescent nanostructures are associated with analyte-binding compounds. Binding of the analyte to the analyte-binding compound changes the photoluminescent properties of the photoluminescent nanostructures. Thus, the presence or absence of the analyte can be determined based on the observed photoluminescent properties of the photoluminescent nanostructures. The change in the photoluminescence can include a change in photoluminescence intensity, a change in peak wavelength, a Raman shift, or a combination thereof.

Single-walled carbon nanotube (SWCNT)-based optical sensors based on noncovalent adsorption of polymer coronas are prepared as colloidal solutions consisting of individualized nanoparticles suspended in water or other solvent. Deployment of these sensors requires either: 1) direct mixing of sensor and sample solutions; or 2) immobilization of sensors onto a solid substrate. While Option 1 is the method of choice for sensor development, it is often not feasible for final sensor deployment as the nanoparticles are more difficult to transport, can contaminate the sample, and/or pose a threat to human health or the environment. As a result, versions of Option 2 have been explored including surface immobilization and hydrogel encapsulation. However, surface immobilization requires functionalized solid substrates (e.g., glass) that are typically expensive, and the performance of hydrogel-encapsulated sensors is susceptible to humidity changes and provide a moist environment for bacterial contamination.

Here, a technique for interfacing SWCNT nanosensors with a paper-based form factor, resulting in superior sensor stability and functionality is described. Paper provides an alternative solid substrate that is lightweight, inexpensive, and can be stored dry. The nanoparticles become immobilized upon being trapped within the porous network and binding to the paper material. Sensors can be interfaced with existing technologies developed in the paper diagnostics field, including manipulation of fluid flow, chemical reaction, and separation. This results in sensor technologies with added versatility and commercial impact relative to previous methods for SWCNT immobilization.

Figure 1:
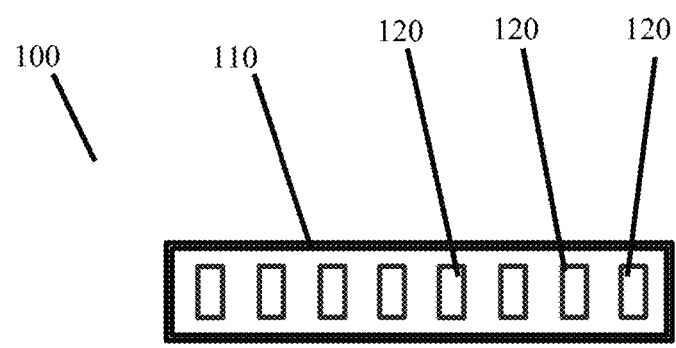
FIG. 1 depicts a sensor.

With reference to FIG. 1, sensor 100 includes a porous planar substrate 110. Sensor 100 includes a plurality of regions 120, each of which can include at least one photoluminescent nanostructure (not shown).

As used herein, the term "porous planar substrate" is given its ordinary meaning in the art and refers to a material that is a porous planar solid. The porous planar substrate can be a fibrous or porous solid material, for example, a woven or non-woven fibrous mat, such as paper, nitrocellulose, nylon or similar material. The porous planar substrate can be dry and, optionally, flexible. The porous planar substrate can wick a liquid and can have the capability to effect a chromatographic separation of the contained materials. The porous planar substrate may include polymer chains that are crosslinked, either directly or via a crosslinking agent. The degree of crosslinking may be varied, in some cases, to tailor the extent to which the gel absorbs or retains fluids. Examples of polymers capable of forming porous planar substrates include, but are not limited to cellulose, nitrocellulose, nylon, poly(ethersulfone), poly(vinylidene fluoride), collagen, silicon-containing polymers, polyacrylamides, crosslinked polymers (e.g., polyethylene oxide, polyAMPS and polyvinylpyrrolidone), polyvinyl alcohol, acrylate polymers (e.g., sodium polyacrylate), and copolymers with an abundance of hydrophilic groups.

The porous planar substrate can be a porous structure. The pore sizes in the porous structure can be determined by factors including the concentration of polymers and crosslinks in the porous planar substrate. A porous planar substrate having a desired pore size or desired pore size distribution can be prepared by selecting the concentrations of monomers and crosslinkers present during polymerization to form a porous planar substrate. It can be advantageous for the porous planar substrate pores to be large enough to permit free access of analytes to components embedded in the porous planar substrate, e.g., to photoluminescent nanostructures. The pore size can be in the range of, for example, 10 nm to 1,000 nm, 20 nm to 500 nm, 50 nm to 250 nm, or 10 nm to 100 nm. When the analyte is a macromolecule (e.g., a protein, such as an immunoglobulin), a pore size greater than 10 nm, greater than 20 nm, greater than 30 nm, greater than 40 nm, greater than 50 nm, greater than 60 nm, greater than 70 nm, greater than 80 nm, greater than 90 nm, or 100 nm or greater can be desirable.

As used herein, the term "nanostructure" refers to articles having at least one cross-sectional dimension of less than about 1 μm, less than about 500 nm, less than about 250 nm, less than about 100 nm, less than about 75 nm, less than about 50 nm, less than about 25 nm, less than about 10 nm, or, in some cases, less than about 1 nm. Examples of nanostructures include nanotubes (e.g., carbon nanotubes), nanowires (e.g., carbon nanowires), graphene, and quantum dots, among others. In some embodiments, the nanostructures include a fused network of atomic rings.

A "photoluminescent nanostructure," as used herein, refers to a class of nanostructures that are capable of exhibiting photoluminescence. Examples of photoluminescent nanostructures include, but are not limited to, single-walled carbon nanotubes ("SWNT"), double-walled carbon nanotubes, semi-conductor quantum dots, semi-conductor nanowires, and graphene, among others. In some embodiments, photoluminescent nanostructures exhibit fluorescence. In some instances, photoluminescent nanostructures exhibit phosphorescence.

If the nanostructure is a carbon nanotube, the carbon nanotube can be classified by its chiral vector (n,m), which can indicate the orientation of the carbon hexagons. The orientation of carbon hexagons can affect interactions of the nanotube with other molecules, which in turn, can affect a property of the nanostructure.

A polymer can be associated with the nanostructure. The association can be a bond, for example, a covalent, ionic, van der Waals, dipolar or hydrogen bond. The association can be a physical association. For example, at least a portion of the nanostructure can be embedded in the polymer or a portion of the polymer can encompass the nanostructure. A polymer can include a polypeptide, a polynucleotide, a polysaccharide or a synthetic polymer. Examples of polysaccharides include dextran and chitosan. A polymer can include a plastic, for example, polystyrene, polyamide, polyvinyl chloride, polyethylene, polyester, polypropylene, polycarbonate, polyacrylamide or polyvinyl alcohol.

A polymer can be biocompatible, which can mean that the polymer is well tolerated by an organism. More specifically, biocompatibility can mean that a polymer does not elicit an immune response when it is brought in contact with an organism. It can also mean that a polymer can integrate into cell structures, cells, tissues or organs of an organism. The organism can be mammal, in particular, a human.

The association of a polymer with a nanostructure can change a property of the nanostructure. The property can be conductivity, polarity, or resonance. The property can be photoluminescence, including fluorescence or phosphorescence. More specifically, the property can be fluorescence with a wavelength in the near infrared spectrum. The property can be an emission wavelength, an emission intensity, a conductance, an electromagnetic absorbance or an emittance.

A polymer can be configured to interact with an analyte. The analyte undergoes a specific and typically reversible binding with an analyte. The analyte can be an ion. The ion can be a metal ion. The metal ion can be a nickel, iron, cadmium, copper, magnesium, calcium, arsenic, lead, mercury or cobalt ion (e.g. $Ni^{2+}$, $Fe^{2+}$, $Cd^{2+}$, $Cu^{2+}$, $Mg^{2+}$, $Ca^{2+}$, $As^{2+}$, $pb^{2+}$, $Hg^{2+}$ or $Co^{2+}$). The polymer can include a protein, a nucleotide, a saccharide, a lipid or combinations thereof. See, for example, WO 2012/030961, which is incorporated by reference in its entirety.

The ion can act a proximity quencher of photoluminescent nanostructure. In particular, the ion can quench near infrared fluorescence. The quenching can be reversible. The quenching can also depend on the distance between the nanostructure and the ion. In other words, as the distance between the nanostructure and the ion changes, the photoluminescence from the nanostructure can also change. Generally, as the distance between the ion and the nanostructure decreases, the amount of photoluminescence quenching can increase. Alternatively, the ion can turn on or enhance fluorescence.

The analyte can bind with a dissociation constant less than 1 mM, less than 0.1 mM, less than 0.01 mM, less than 1 µM, less than 0.1 µM, or less than 0.01 µM. A first binding partner and a second binding partner can bind with a dissociation constant greater than 1 nm, greater than 0.01 µM, greater than 0.1 µM, greater than 1 µM, greater than 0.01 mM, or greater than 0.1 mM.

The interaction of an analyte with a capture protein that is interacting with a polymer associated with a nanostructure can change a property of the nanostructure. The property can be conductivity, polarity, or resonance. The property can be photoluminescence, including fluorescence or phosphorescence. More specifically, the property can be a fluorescent emission within the near infrared spectrum. The property can be an emission wavelength, an emission intensity, a conductance, an electromagnetic absorbance or an emittance.

The analyte can be a small molecule, protein, biomolecule, drug, biologic, or a metabolite thereof. For example, the analyte can be a monosaccharide, a polysaccharide, an amino acid, peptide, polypeptide, protein, a nucleotide, an oligonucleotide, a lipid, a polylipid, or a combination thereof. As one example, the analyte can be immunoglobulin G (IgG) and the capture protein can be selected to specifically bind IgG. In this case, the capture protein can be, for example, protein A or *Pisum sativum* agglutinin (PSA).

A method of detecting an analyte can include determining the presence of an analyte in the sample based on the monitored property. Determining the presence of an analyte can include evaluating when the analyte is absent. In some embodiments, determining the presence of an analyte can include determining the concentration of the analyte, determining the purity of the analyte or determining the quantity of the analyte. In some embodiments, relatively low concentrations or quantities of an analyte can be determined. The ability to determine low concentrations of an analyte may be useful, for example, in detecting trace pollutants or trace amounts of toxins within a subject. In some embodiments, analyte concentrations of less than about 100 micromolar, less than about 10 micromolar, less than about 1 micromolar, less than about 100 nanomolar, less than about 10 nanomolar, or less than about 1 nanomolar can be determined. The quantity of the analyte that can be determined can be less than 1 mole, less than 1 millimole, less than 1 micromole, less than 1 nanomole, less than 1 picomole, less than 1 femtomole, less than 1 attomole or less than 1 zeptomole. In some cases, a single molecule of an analyte can be determined. The purity of the analyte can be greater than 25% pure, greater than 50%, greater than 75% pure, greater than 80%, greater than 85% pure, greater than 90%, greater than 95% pure, greater than 99% pure or greater than 99.9% pure.

A sensor array can include a plurality of analysis regions on a support. In some embodiments, the plurality of analysis regions can include two or more subsets of analysis regions. For example, a first subset of analysis regions can differ from a second subset of analysis regions by including a different nanostructure, a different linker, a different binding partner, a different capture protein, a different analyte or a different sample. Additionally, a first subset of analysis regions can differ from a second subset of analysis regions by including a different photoluminescent nanostructure or including a different environmental factor including a buffer, a reagent, a nutrient, a serum, an exposure to light, an oxygen concentration, a temperature or a pH.

In general, a sensor can include a porous planar substrate and at least one photoluminescent nanostructure on or embedded within the porous planar substrate.

In another aspect, a method of detecting an analyte can include contacting a composition including an analyte to a sensor including: a porous planar substrate and a photoluminescent nanostructure on the porous planar substrate.

In some embodiments, the method of detecting the analyte can further include detecting photoluminescence from the photoluminescent nanostructure.

In another aspect, a sensor for detecting one or more analytes can include a porous planar substrate, and at least one photoluminescent nanostructure on or embedded within the sensor porous planar substrate.

In certain circumstances, the sensor can include an analyte-binding compound associated with the photoluminescent nanostructure.

In certain circumstances, the photoluminescent nanostructure can include a polymer. The polymer can include a polypeptide, a polynucleotide or a polysaccharide. In certain circumstances, the polymer can be a polynucleotide. The polymer can include a combination of these components.

In certain circumstances, the sensor can include a plurality of regions on the porous planar substrate, at least one of the plurality of regions includes a first region including the at least one photoluminescent nanostructure. The plurality of regions can include a second region including at least one photoluminescent nanostructure different from the at least one photoluminescent nanostructure.

In certain circumstances, the sensor can include a plurality of regions including two, three, four, five, six, seven, eight, nine, ten, eleven, twelve or more distinct regions. Each distinct region can include a different photoluminescent nanostructure or composition. The regions can be patterned into a one dimensional, two dimensional or three dimensional array. The one dimensional array can be a line having fixed spacing (regular or irregular). The two dimensional array can be a grid having fixed spacing (regular or irregular).

In certain circumstances, the porous planar substrate can include a paper, nitrocellulose, or nylon, or combinations thereof.

In another aspect, a method of making a sensor for detecting one or more analytes can include depositing a photoluminescent nanostructure on or within a porous planar substrate.

In certain circumstances, the method can include patterning the porous planar substrate to include a plurality of regions, at least one region receiving the photoluminescent nanostructure.

In certain circumstances, the method can include depositing includes placing a liquid including the photoluminescent nanostructure on the porous planar substrate.

In another aspect, a method of detecting an analyte can include contacting a sensor including a photoluminescent nanostructure on or embedded within the porous planar substrate with a sample; and detecting an output from the sample to determine the presence of the analyte. The method can include comparing an output of the sensor before contact with the sample with the output of the sensor after contact with the sample. The output and comparison can be subjected to principle component analysis to deconvolute the presence of multiple analytes in a sample.

In certain circumstances, the method can include measuring the output at two or more regions of the porous planar substrate.

In certain circumstances, the method can include moving the porous planar substrate relative to a detector.

In certain circumstances, the method can include moving the porous planar substrate relative to a detector at a controlled rate. The controlled rate can be a constant rate or another reproducible rate to permit comparison of data from a sample and a control for a given sensor.

In another aspect, a system for detecting an analyte can include a platform including a sample holder, a detector including a directed at the platform, and a translation stage including an axis of motion orthogonal to the contacting a sensor including a photoluminescent nanostructure on or embedded within the porous planar substrate with a sample.

In certain circumstances, the system can include a translation stage moves the platform at a controlled rate.

In certain circumstances, the system can include an photoexcitation device.

Technical Description

Sensor Immobilization: Sensors are immobilized on paper using the drop casting method illustrated in FIG. 2A. Briefly, SWCNT solution is added atop the paper and allowed to spread into the material. Once dried, the paper is washed under light agitation to remove unbound nanosensors. Following this washing step, the paper-immobilized sensors are dried and stored. Immediately prior to the experiment, the sensors are wetted and fixed to a solid support, after which fluorescence is collected using existing instrumentation.

Figure 2A:
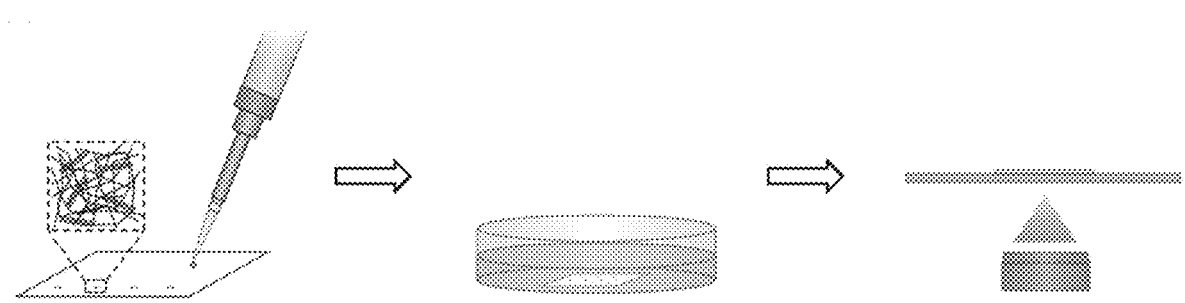
FIG. 2A-2C depict data collected from a sensor described herein.
Figure 2B:
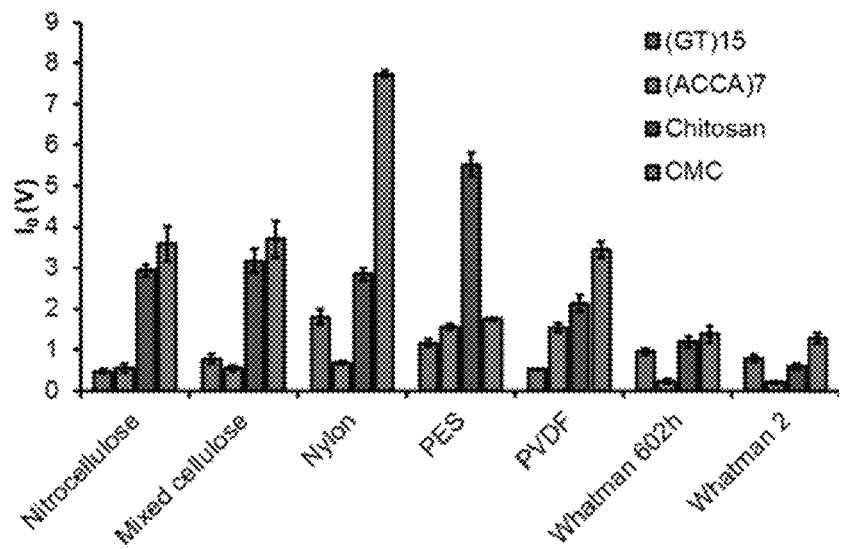
Figure 2C:
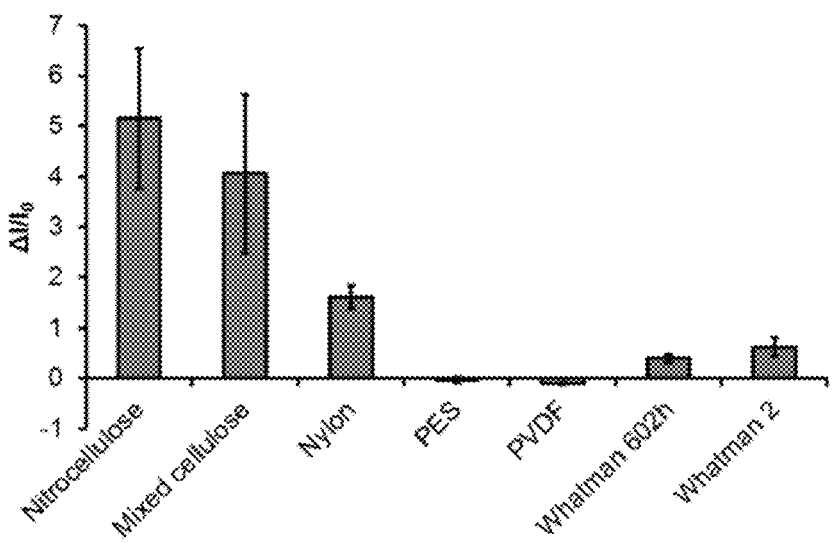

The experimental technique described by FIG. 2A has been successful in immobilizing a variety of SWCNT sensors on many different paper materials. FIG. 2B presents the fluorescence signals for nanoparticles wrapped with ssDNA ($(GT)_{15}$ and $(ACCA)_7$), chitosan, and carboxymethylcellulose deposited on seven different paper materials. The sensors remain fluorescent upon paper immobilization. Seven different paper substrates and four SWNT wrappings were tested. About 3 μL of ~10 mg/L SWNT solutions were deposited. Variation in this starting signal among SWCNT wrappings and paper materials is a result of the paper pore size and chemical properties. In addition, the paper material choice can augment sensor responsivity, as shown in FIG. 2C for $(ACCA)_7$-wrapped SWCNTs against a probe analyte, ascorbic acid. While $(ACCA)_7$-wrapped SWCNTs display a fluorescence turn on response to ascorbic acid when dispersed in solution, FIG. 2C indicates that the magnitude of the normalized fluorescence change is influenced by the paper material. See, also, FIG. 24.

Figure 3A:
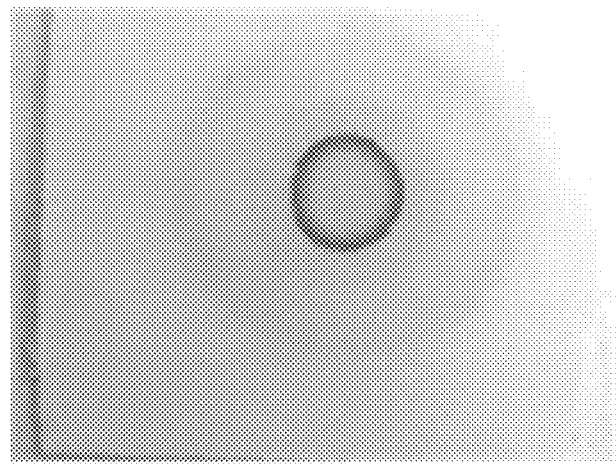
FIG. 3A-3I depict systems, sensors and systems described herein.
Figure 3B:
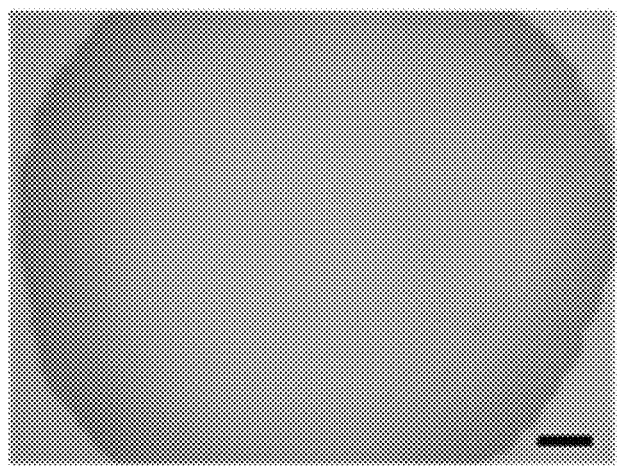
Figure 3C:
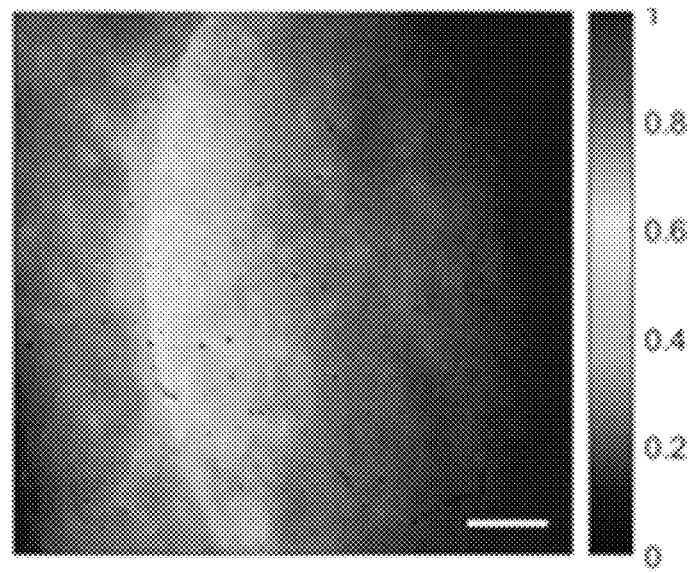
Figure 30:
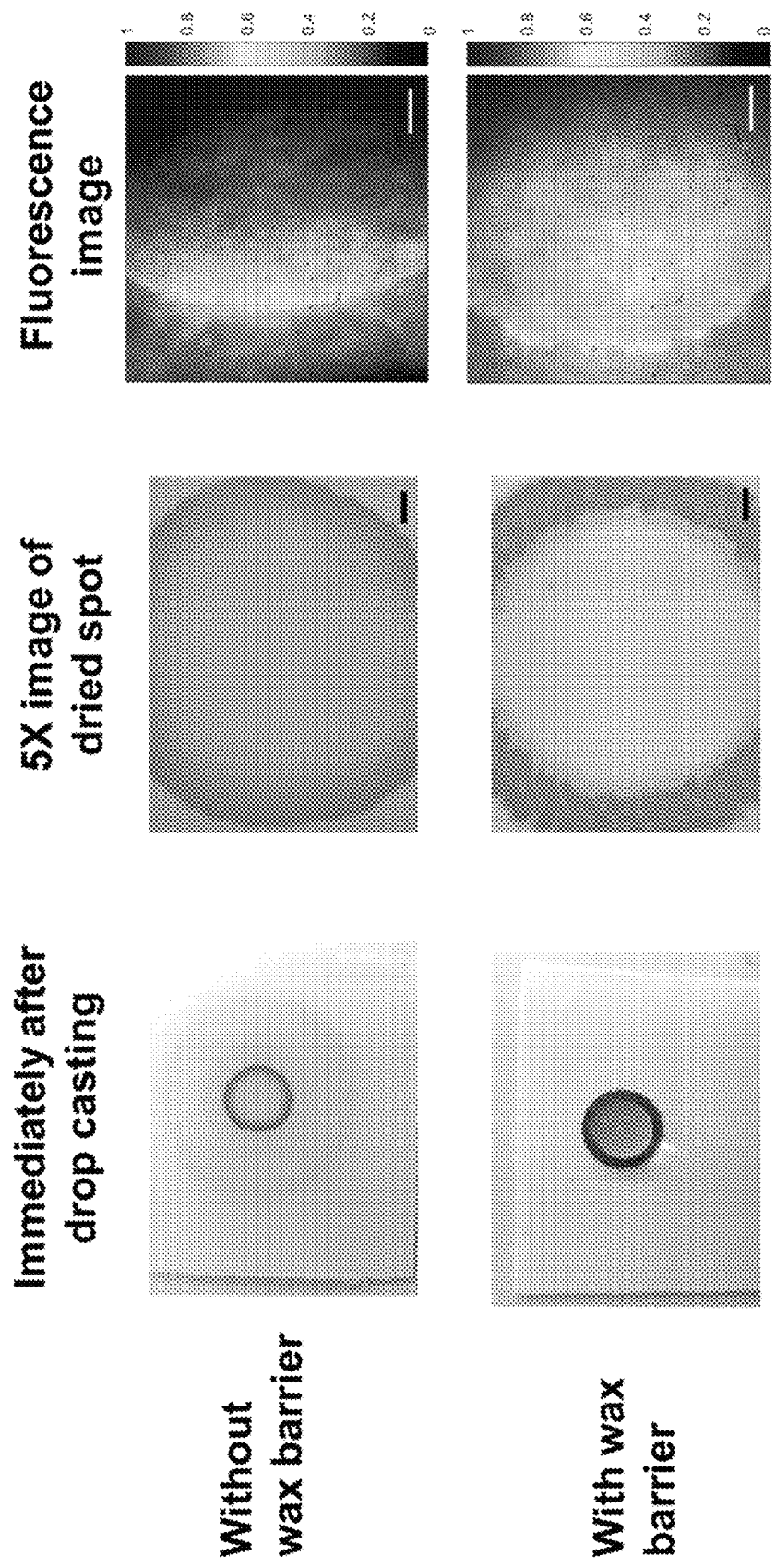
Figure 31:
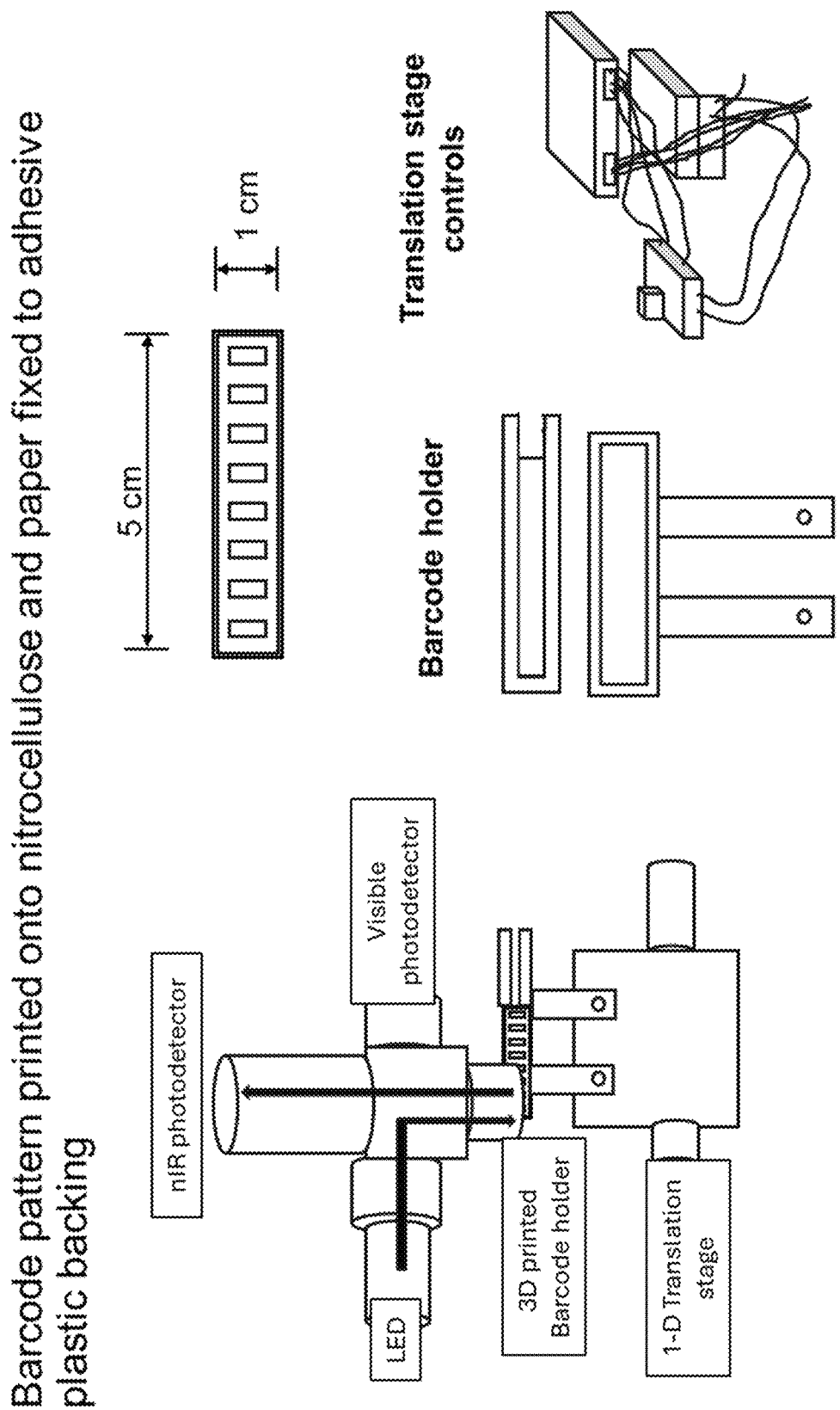

Surface Patterning: Sensors can be patterned onto paper substrates using one or more techniques including photolithography, inkjet printing, paper cutting and wax printing. FIGS. 29-30 provide an overview of adapting the wax printing method for patterning nanosensors onto nitrocellulose. Patterning SWNTs onto paper using wax printing method can enhance sensor functionality. Briefly, patterns are generated and printed onto nitrocellulose using a Xerox ColorQube wax printer. The paper is baked to re-melt the wax and allow it to penetrate into the nitrocellulose pores, forming hydrophobic barriers. FIGS. 3A-3C show optical and fluorescence images of the sensor spot that is formed in the absence of a wax barrier, which results in an uneven distribution of sensors. Upon addition of a wax barrier, a droplet of sensor solution is contained, which results in a more even distribution and customizable dimensions for the sensor region. FIG. 30 shows images immediately after drop casting, a 5× image of dried spot, a fluorescence image of samples without wax barrier and with wax barrier. The results suggest that a wax barrier can result in more uniform SWNT distribution and that printing and baking process does not reduce SWNT binding ability.

FIG. 2A depicts a schematic of drop-casting technique for sensor immobilization on paper. FIG. 2B depicts a fluorescence intensity, $I_0$, of various SWCNT-polymer hybrids immobilized on different paper substrates. FIG. 2C depicts an image of paper material on the normalized fluorescence change of $(ACCA)_7$-wrapped SWCNT to ascorbic acid.

Figure 3D:
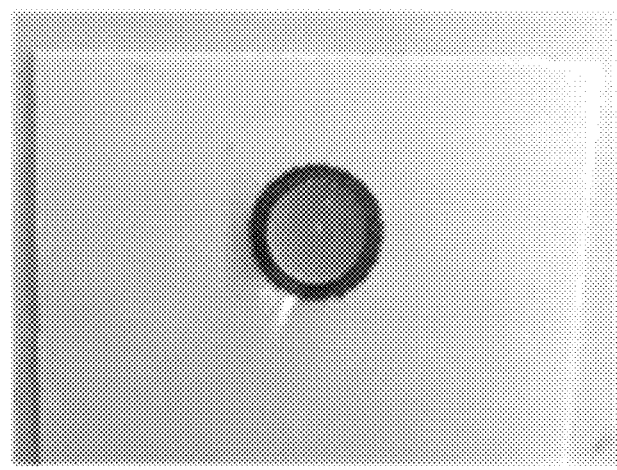
Figure 3E:
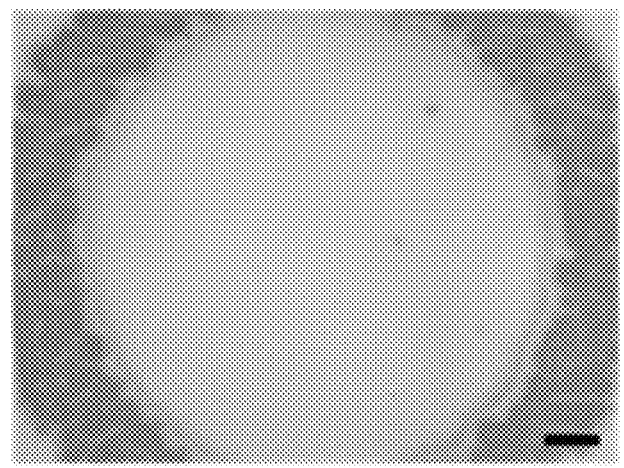
Figure 3F:
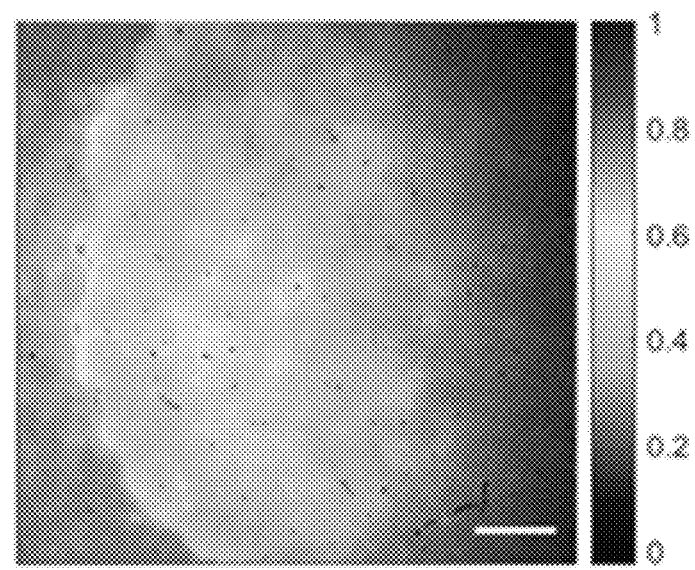
Figure 3G:
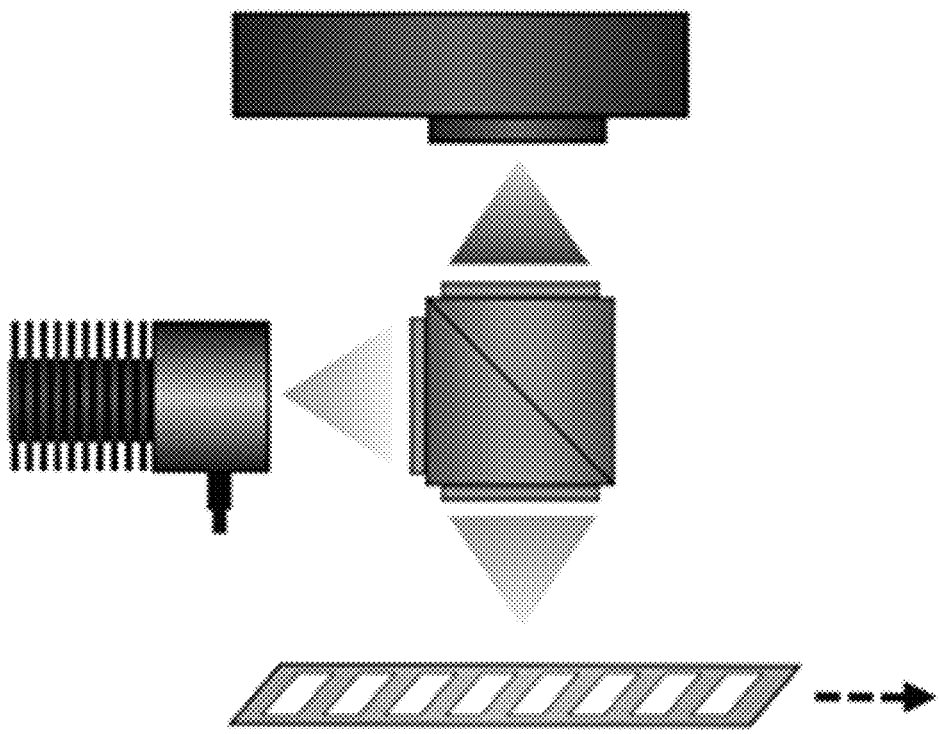

The patterning of paper substrates provides added sensor functionality including the control of fluid flow and chemical separation. Additionally, it enables facile multiplexing via the deposition of multiple sensors on a single paper slab. FIG. 3G provides a schematic of an instrument setup we have built for reading sensor "barcodes," or 1-dimensional sensor arrays (additional details on instrumentation components and operation can be found in supplemental information). Briefly, sensor signals are collected using commercially available photodetectors attached to a custom optomechanical setup with readouts collected using a LabJack U6 Pro running standard code.

Figure 3H:
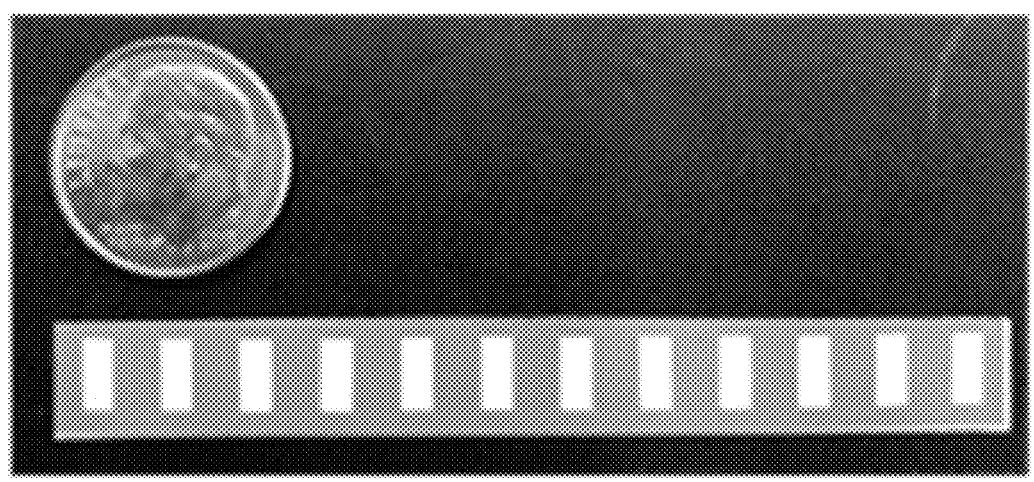

Sensor operation: The sensor barcode is fixed to a translation stage that moves beneath the static optics, resulting in a time-dependent signal that can be correlated with barcode position. The size of the sensor barcodes is shown in FIG. 3H and the barcodes are fixed to a plastic backing card to provide rigidity.

Figure 3I:
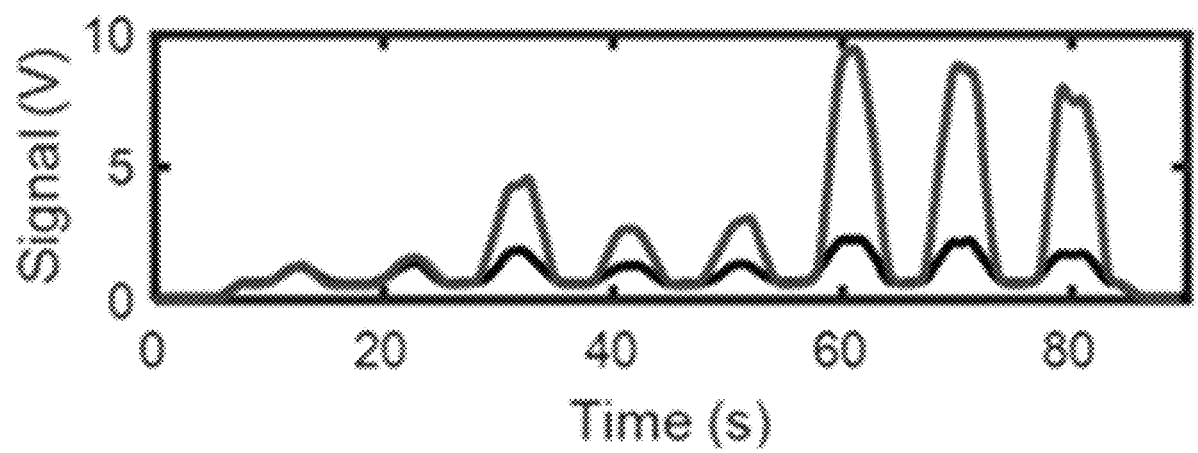

Sensor barcodes are fabricated by printing the barcode patterns onto nitrocellulose and baking the nitrocellulose at 105° C. for 10 minutes. Barcode pieces are cut out and fixed to a plastic backing card typically used for lateral flow assays. SWCNT sensor solutions are deposited onto the white, exposed regions of the nitrocellulose and allowed to bind for several minutes at room temperature. The barcodes are later washed in water and measured using our custom-built instrumentation. FIG. 3I provides the barcode reading before (black) and after (red) dipping the barcode into 10 mM ascorbic acid. From left to right, peaks 1 and 2 are blanks and peaks 3-8 represent distinct SWCNT sensors.

FIG. 3A depict image of sensor spot immediately after depositing solution without wax barrier. FIG. 3B depict 5× Optical and FIG. 3C fluorescence image of sensor spot without wax barrier. FIG. 3D depicts the image of sensor spot immediately after depositing solution with wax barrier. FIG. 3E depicts 5× Optical and FIG. 3F fluorescence image of sensor spot with wax barrier. FIG. 3G depicts custom-built experimental setup for collecting sensor barcode measurements. FIG. 3H depicts image of sensor barcode fixed to plastic backing. FIG. 3I depicts sensor barcode fluorescence measurement before (black) and after (red) dipping barcode in ascorbic acid solution.

Advantages and Improvements

Paper-immobilization of SWCNT-based optical sensors offers numerous advantages over other sensor form factors. These advantages include, but are not limited to:

Storage and transportation: SWCNT-based sensors are prepared as concentrated, metastable colloidal solutions that are typically diluted immediately prior to measurement collection. These solutions must be kept airtight to limit evaporation and are often stored at 4° C. to limit sensor aggregation over time. Paper-immobilized sensors can be stored dry at room temperature and are much more lightweight, making transportation easier.

Sensor stability: We have demonstrated that paper-immobilized sensors remain stable after being stored dry at ambient conditions for nearly 60 days. This is shown in FIGS. 4A-4F for nitrocellulose, nylon and mixed cellulose-bound SWCNTs, where sensors were fabricated at MIT and transported internationally. Sensors transported internationally performed identically to those stored at MIT, and the response to ascorbic acid remained stable up to two months after fabrication.

Compatibility with existing paper diagnostic technologies: Paper diagnostics is a well-developed field that has resulted in many innovations pertaining to the manipulation of fluid flow, performance of chemical reactions, and the separation of complex mixtures. These innovations can be directly interfaced with immobilized SWCNT sensors, significantly increasing the functionality and impact of this invention.

Ease of multiplexing: Paper patterning techniques, including the wax printing method, make sensor multiplexing very simple. The sensor barcode technology can enable rapid detection of multiple analytes.

Accessibility of other solvent systems: SWCNT-based sensor solutions are typically prepared in water, which limits their deployment to water-based systems. Fabrication of sensors in alternative solvent systems would require redesign of the polymer wrapping, and thus, a change in the sensor response properties. Given that paper-immobilized SWCNTs are stored dry, the sensors can be wetted by other solvents including oil and maintain fluorescence. This opens the opportunity for sensor development in other solvent systems of interest.

Figure 4A:
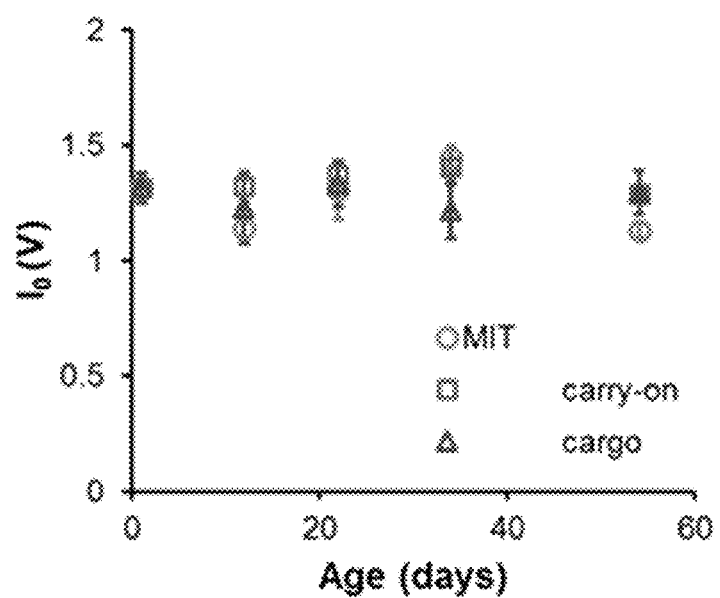
FIGS. 4A-4F depict data collected from a sensor described herein.
Figure 4B:
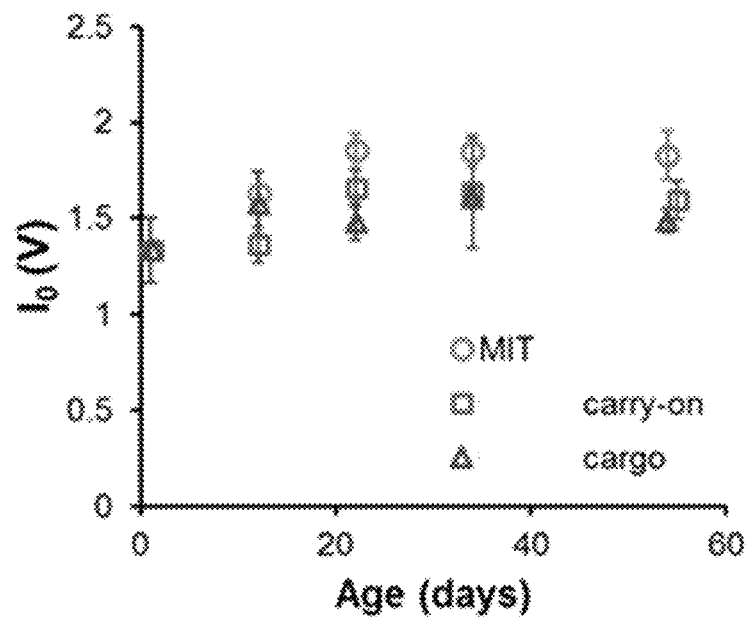
Figure 4C:
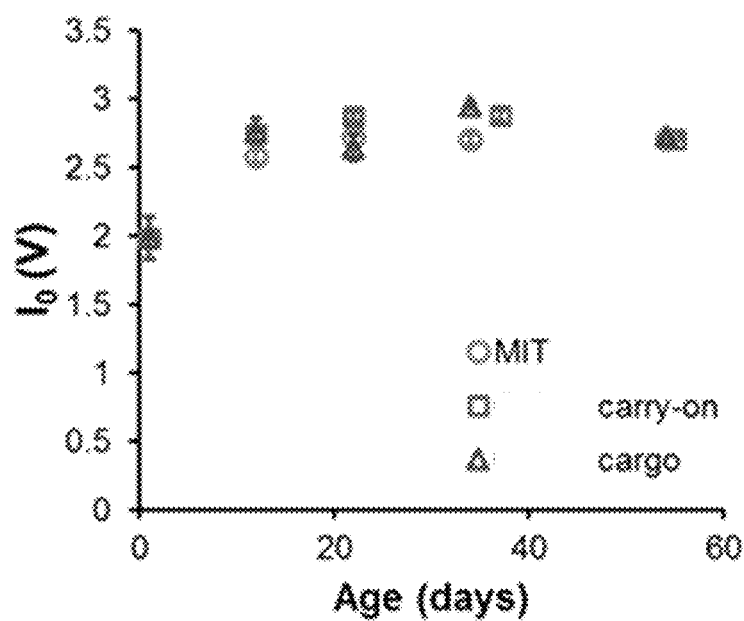
Figure 4D:
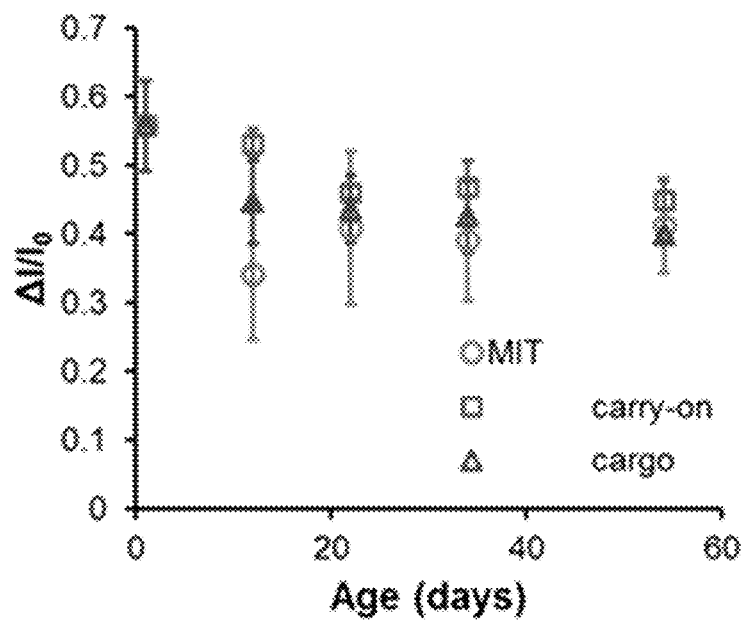
Figure 4E:
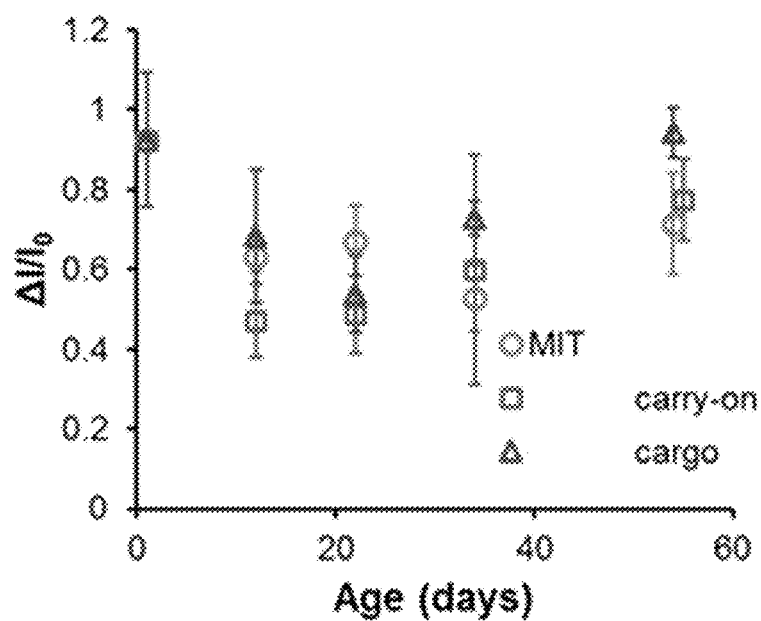
Figure 4F:
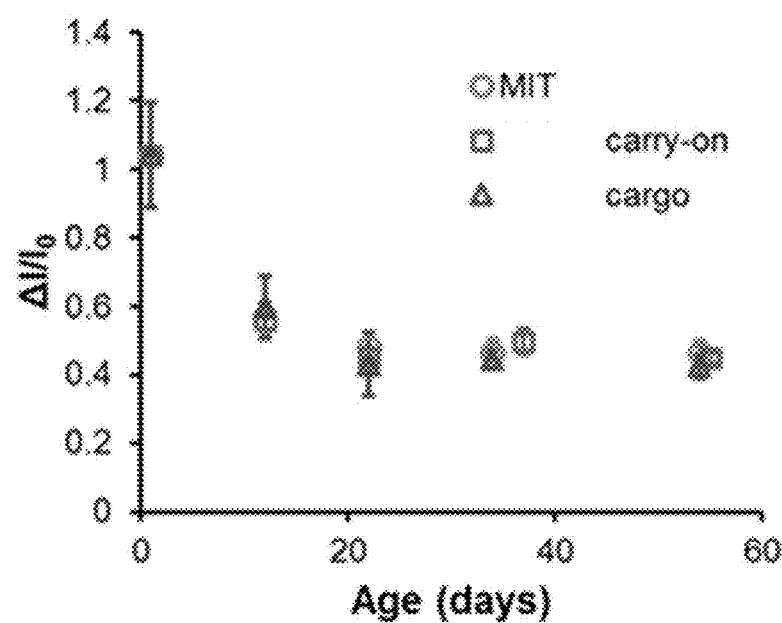

FIGS. 4A-4C depict starting fluorescence intensity and FIGS. 4D-4F depict response to 10 mM ascorbic acid for paper-immobilized SWCNTs over the course of nearly 60 days. Samples were either stored at MIT, transported internationally through carry-on luggage, or transported internationally through cargo luggage. Paper materials tested include nitrocellulose (FIG. 4A, FIG. 4D), nylon (FIG. 4B, FIG. 4E), and mixed cellulose (FIG. 4C, FIG. 4F).

Commercial Applications (Economic Potential, Etc.)

This technology provides a new form factor for SWCNT-based optical sensors that better enables their deployment for a variety of applications including, but not limited to:

In vitro diagnostics: Paper is already used in IVD devices as part of lateral flow assays and other similar technologies. SWCNT-based sensors that have been developed for various biomarkers of interest can be immobilized and deployed in a similar manner.

Food and water contaminant monitoring: Paper represents a convenient and inexpensive form factor for sensor deployment throughout the food supply chain. The ease of sensor multiplexing is particularly advantageous as the list of potential contaminants is very large.

Biopharmaceutical characterization: SWCNT-based sensors have been developed for rapid biopharmaceutical characterization during the manufacturing process. Moreover, paper-immobilized sensors could be used to query sample fidelity in the clinic prior to administration.

Chemical sensors within manufacturing processes: Paper-immobilized sensors can be developed as part of a "dipstick" type assay for chemical characterization or for continuous process monitoring.

Figure 5A:
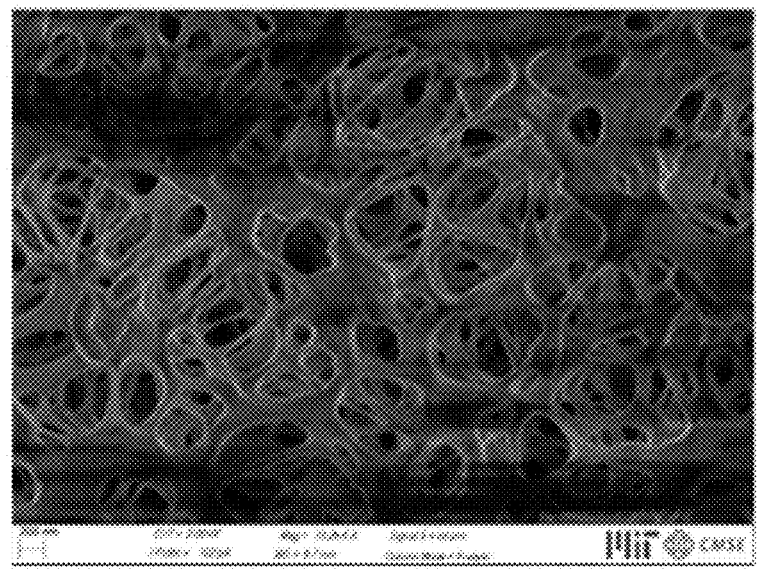
FIGS. 5A-5C depict micrographs.
Figure 5B:
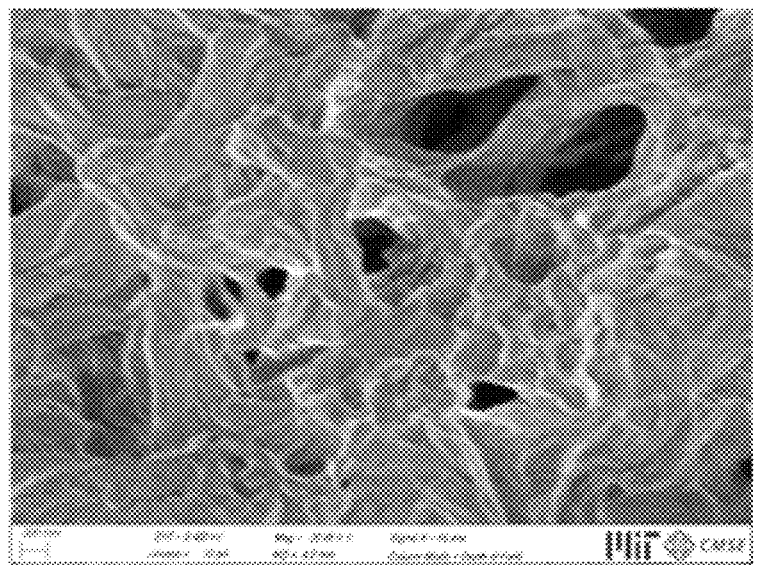
Figure 5C:
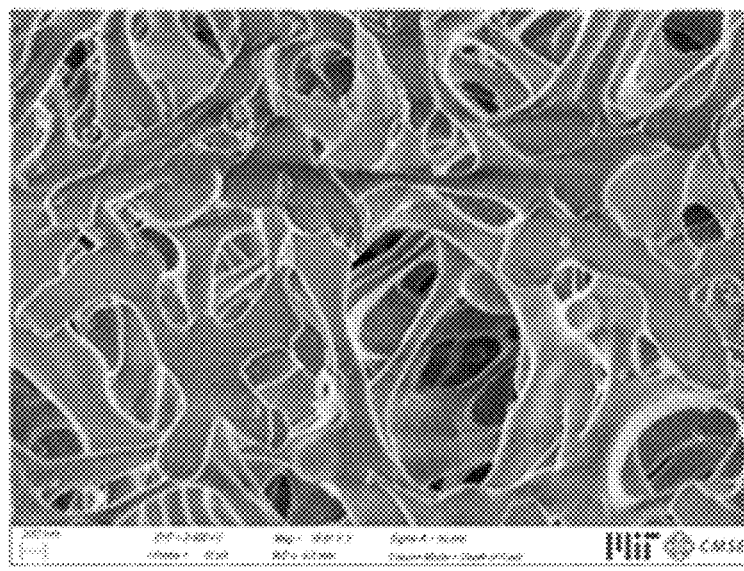

FIGS. 5A-5C depict SEM images of (FIG. 5A) blank nitrocellulose, (FIG. 5B) $(GT)_{15}$-wrapped SWCNTs immobilized on nitrocellulose, (FIG. 5C) $(GT)_{15}$-wrapped SWCNTs immobilized on nitrocellulose and blocked with 5% milk solution.

Figure 6A:
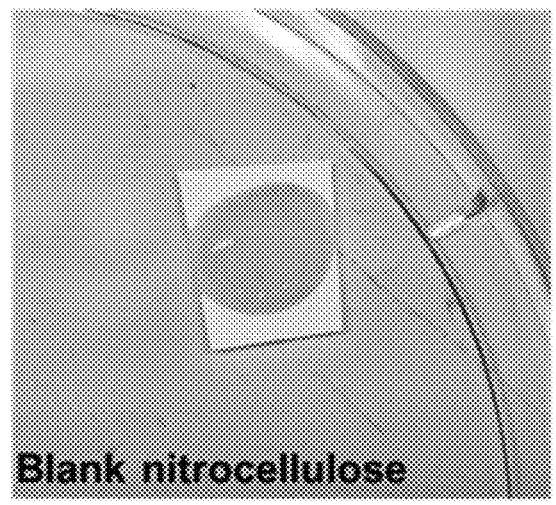
FIGS. 6A-6C depict data collected from a sensor described herein.
Figure 6B:
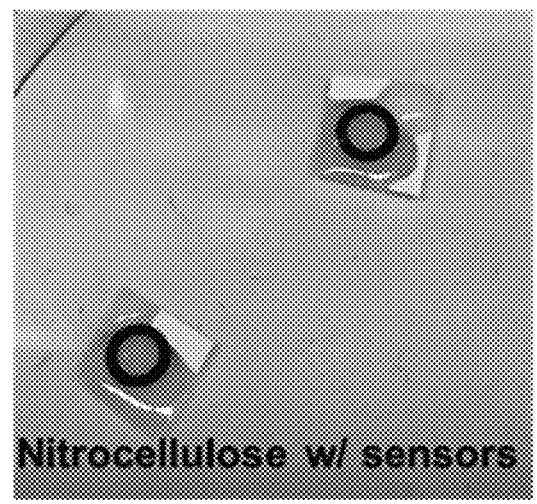
Figure 6C:
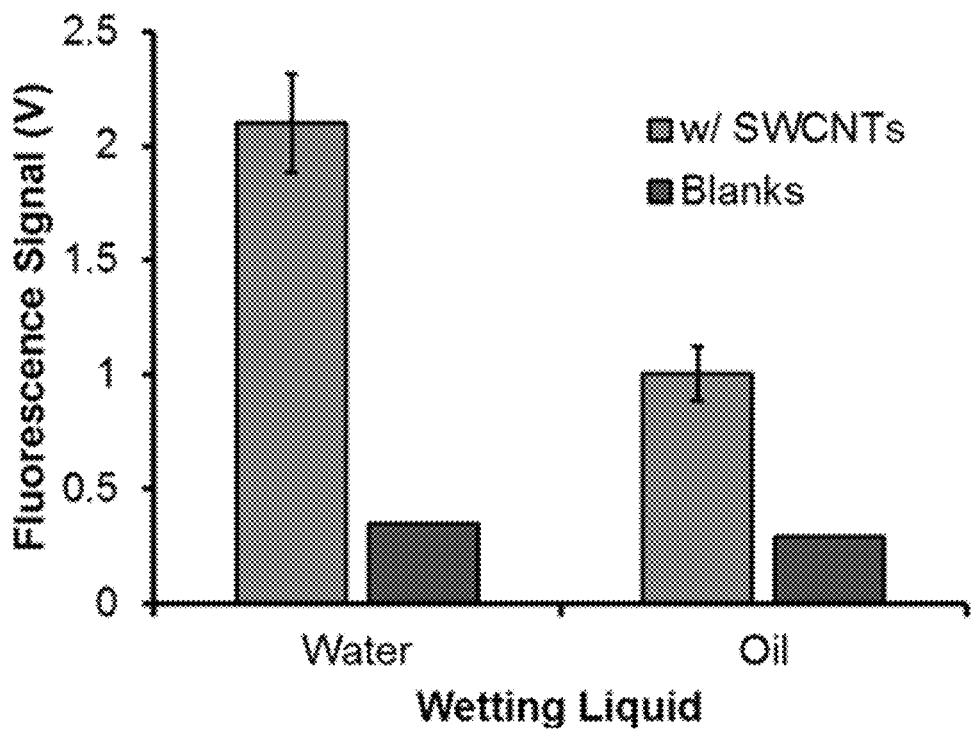

FIGS. 6A-6C depict extending SWCNT-based sensors to nonaqueous solvent systems. FIG. 6A shows wetting of nitrocellulose by canola oil. FIG. 6B shows wetting of nitrocellulose-immobilized SWCNTs by canola oil. FIG. 6C shows fluorescence signal of nitrocellulose-immobilized SWCNTs in water and canola oil.

Figure 7A:
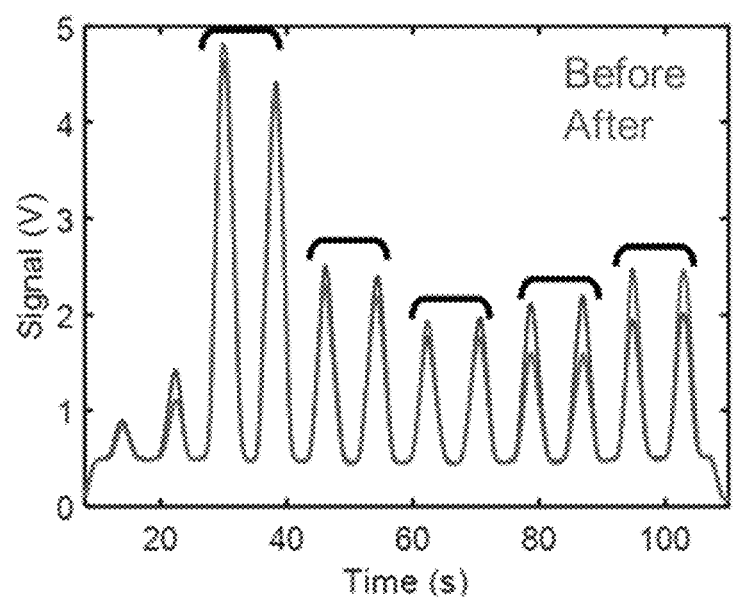
FIGS. 7A-7C depict data collected from a sensor described herein.
Figure 7B:
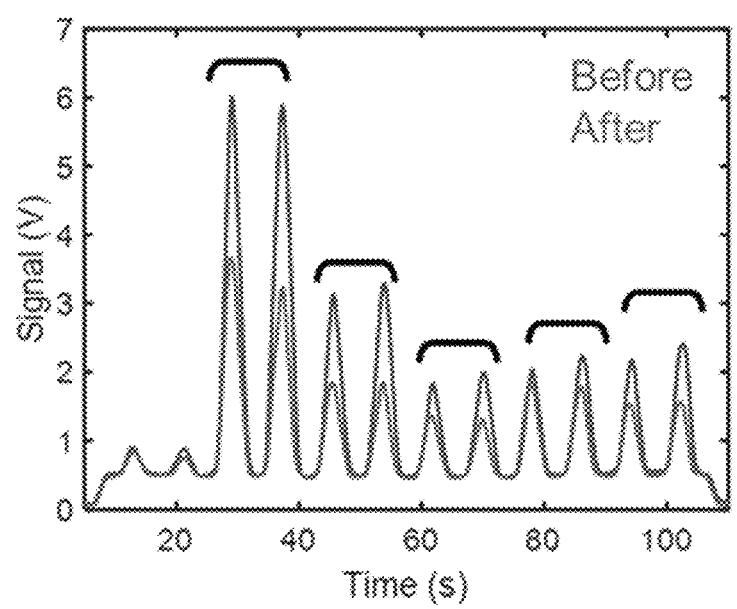
Figure 7C:
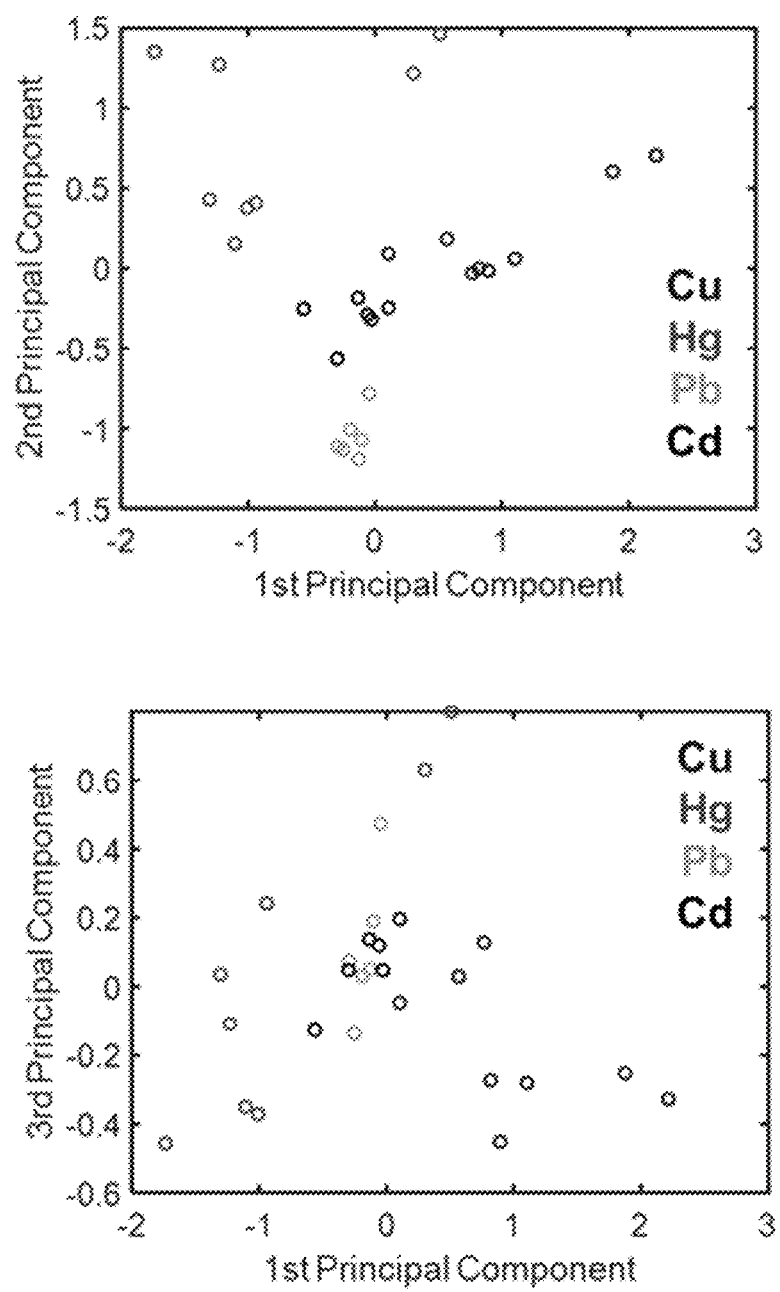

FIGS. 7A-7C depict fluorescence signal of sensor barcodes before (blue) and after (red) the addition of (FIG. 7A) 100 µM Hg and (FIG. 7B) 100 µM Cu. Black brackets represent replicates of individual sensors and the two leftmost peaks are blanks. FIG. 7C depicts principal component analysis of sensor barcode measurements demonstrating the ability to distinguish four different metal ions.

Figure 8:
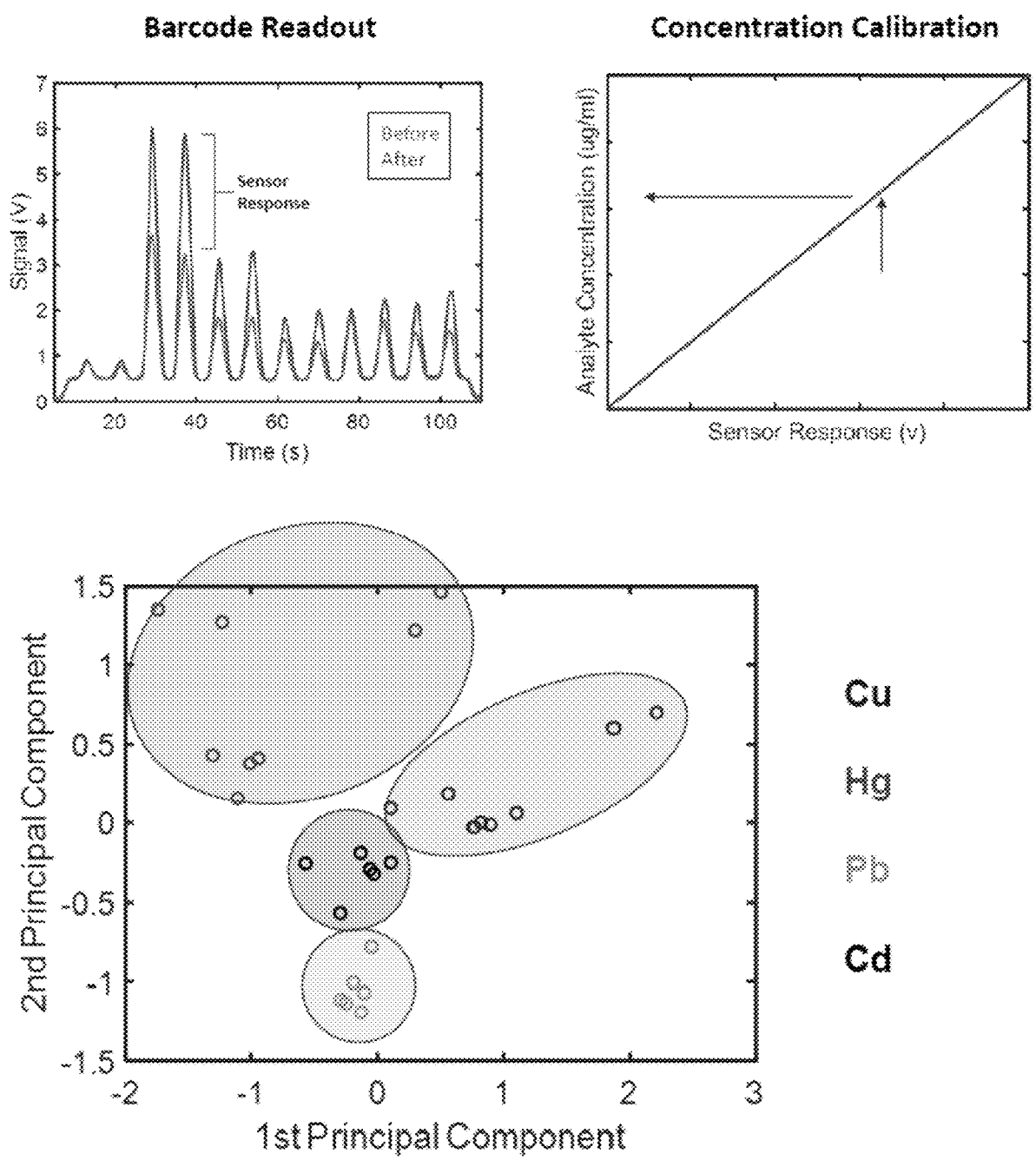
FIG. 8 depicts data collected from a sensor described herein.

Referring to FIG. 8, there exists a need for rapid, quantitative and low cost sensors along the food supply chain. Carbon nanotube based optical sensors offer novel capabilities to multiplex detection of different classes of adulterants. The sensor being a paper form factor allows for the development of economical portable devices.

SWCNT sensor barcodes are composed of ssDNA-wrapped SWCNTs patterned onto nitrocellulose via the printing of hydrophobic barriers. The following protocol outlines the various steps involved in the fabrication and measurement of the barcodes.

SWCNT Dispersion Using Specific ssDNA Oligonucleotides sDNA-SWCNT dispersions were prepared by combining 1 mg of SWCNTs and 2 mg ssDNA in 1 mL of 100 mM NaCl. This mixture was tip sonicated in an ice bath with a 0.125 in. probe for 10 minutes at a power of 4 W. Crude SWCNT dispersions were centrifuged twice at 16,000 g for 90 min, with the top 80% of supernatant being collected after each round of centrifugation. Absorption spectra of SWCNT dispersions were collected to approximate the concentrations of the stock solutions.

Barcode Fabrication Using the Wax Printing Method

The wax printing technique was adapted from the procedure outlined by Lu et al. (*Analytical Chemistry* 82 2010). Briefly, a Xerox ColorQube 5780 wax printer was used to print barcode patterns onto nitrocellulose. The paper was later baked in an oven at 105° C. for 10 minutes to allow the wax to melt into the porous nitrocellulose matrix. Upon cooling, individual barcodes were cut out and fixed to a plastic backing card traditionally used for lateral flow assays. SWCNT solutions at a concentration of 5-20 mg/L were deposited onto the exposed regions of nitrocellulose and allowed to bind for a specified period of time, after which they were submerged in water to wash away unbound SWCNTs. Barcodes were measured the same day that they were fabricated and were stored submerged in water to minimize oxygen exposure.

Barcode Measurements

To perform barcode measurements, a one-dimensional translation stage was positioned below a static, single-channel optical setup and controlled via an external circuit board. A barcode holder was 3D printed and fixed to the translation stage to accurately and consistently position the barcodes during each experiment. Fluorescence measurements are performed before and after submerging the barcode in analyte solution. During each measurement, nIR fluorescence is collected as the barcode is translated at a constant velocity beneath the optical setup. Peaks in the time-dependent fluorescence data correspond to sensor regions of the barcode, which allows us to correlate the peak signals to barcode position and specific sensors. Each barcode contains an identifying mark in the top left corner in order to ensure it is read in the proper direction. Upon collecting the initial fluorescence signal, the barcode is submerged in analyte solution for a specified period of time (1-5 minutes) after which it is measured again.

Analyzing Barcode Data

Barcode measurements collected before and after analyte addition are analyzed using a Matlab script. Briefly, the maximum fluorescence intensity of each peak is extracted and correlated to position on the barcode. Fluorescence values are background corrected using the peak signal from barcode regions left blank (i.e., no SWCNTs). The maximum fluorescence signals from each sensor region are used to calculate the normalized sensor response, R, according to the following equation:

$$R = \frac{I_{final} - I_{initial}}{I_{initial}}$$

where $I_{initial}$ and $I_{final}$ are the fluorescence intensities collected before and after interaction with the analyte, respectively.

A database was created to store the sensor responses for various analytes and ssDNA wrappings. These data can be used to develop a sensor binding model using a first principles approach, or can be analyzed using alternative techniques such as principle component analysis (PCA). To analyze the data using PCA, we use Matlab's built-in PCA algorithm and input a matrix of response data where the columns of the matrix are unique sensors (i.e., unique ssDNA wrappings) and each row is a particular "experiment" (i.e., a replicate for a given analyte). Based on the PCA results, we plot each data point in principal component space and color each data point according to the analyte tested. This allows us to compare the resulting clustering to the identities of the analytes. Moreover, the PCA analysis allows us to identify which sensors provide the best discriminatory ability for a given set of analytes, which can serve as a guide for barcode design.

Systems and data are shown in FIGS. 9-35.

FIG. 9 shows deployment of SWNT sensors requires some form of sensor immobilization. One option is solution phase deployment, in which sensors are dispersed in solution with analyte. This approach is currently limited to waterbased systems. In this approach, the resulting SWNT solution is treated as hazardous waste. Another option is hydrogel encapsulation, in which sensors are immobilized within a porous hydrogel network. This approach is currently limited to water-based systems. It is unclear how sensor performance is affected by drying, microbial contamination, or other factors. A third option is surface immobilization, in which sensors are immobilized on a functionalized glass or plastic surface. The strength of surface immobilization can be sensitive to analyte solution properties (e.g., pH). The necessary functionalized substrates may be costly (>$5 for slide).

The approach adopted here is paper immobilization, which has not been reported for SWNT-based optical sensors before this work. Sensors are immobilized within a paper/membrane fibrous network and stored dry. The approach is compatible with water-based and oil-based systems. The paper immobilization approach can have potential advantages, including being lightweight, inexpensive, can be stored dry and can include additional sensor functionality.

FIG. 10 shows advantages of paper form factor, which can include inexpensive substrate for sensor immobilization (<$0.03 per square cm from Sigma Aldrich), ease of storage and transport, can be stored dry at various temperatures and humidities and the approach is already implemented in medical diagnostics and other routine chemical tests, meaning the paper sensor can interface with existing laboratory instrumentation for collecting sensor measurements.

Figure 11:
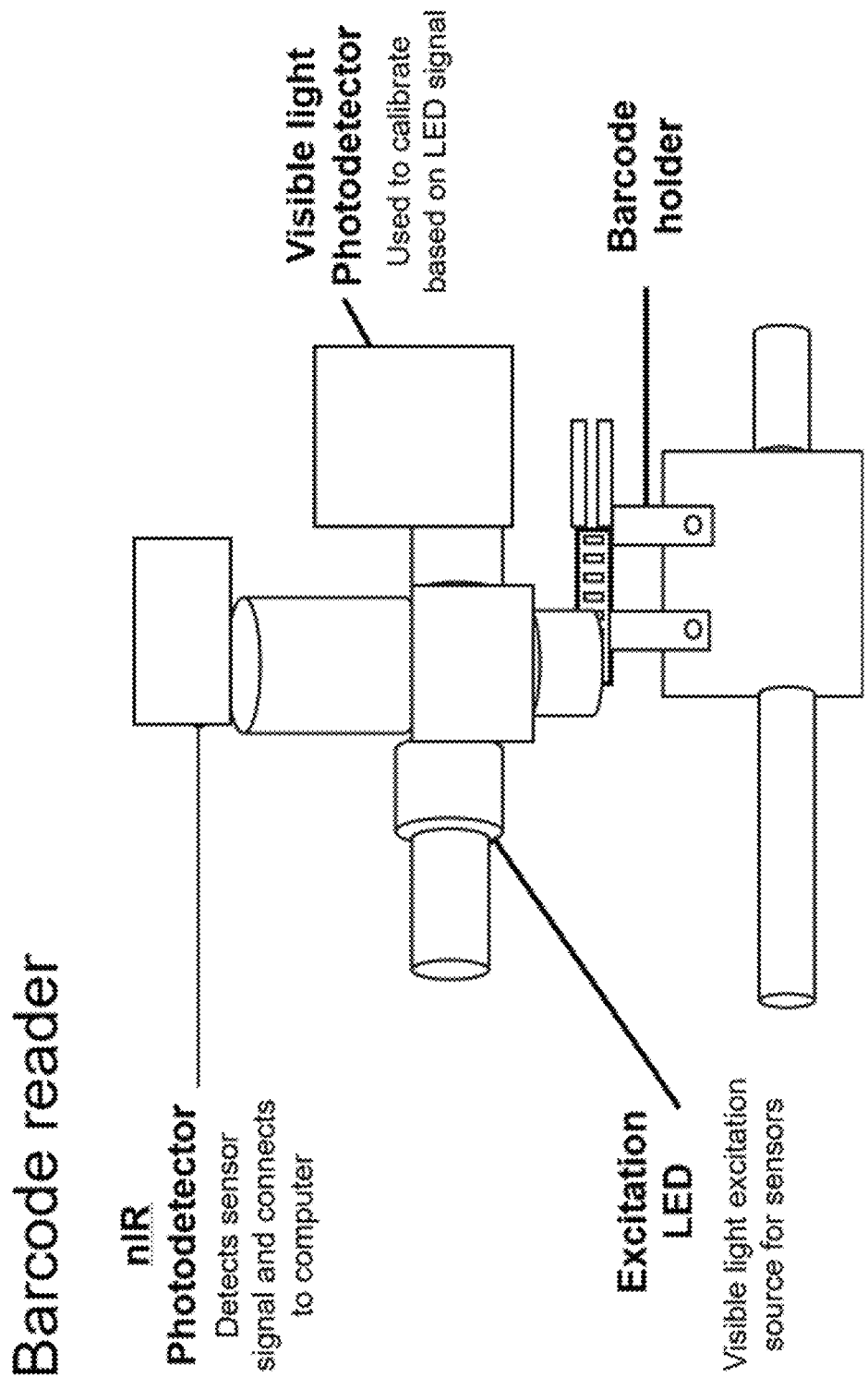

FIG. 11 shows a barcode reader, which can include a nearIR photodetector, which detects a sensor signal and connects to a computer. The reader can include a photodetector used to calibrate based on LED signal, and photoexcitation source, such as an LED or other visible light excitation source for sensors. The reader can include a barcode holder, which can be stationary or can be moved in one dimension or two dimensions using a translation stage.

Figure 12:
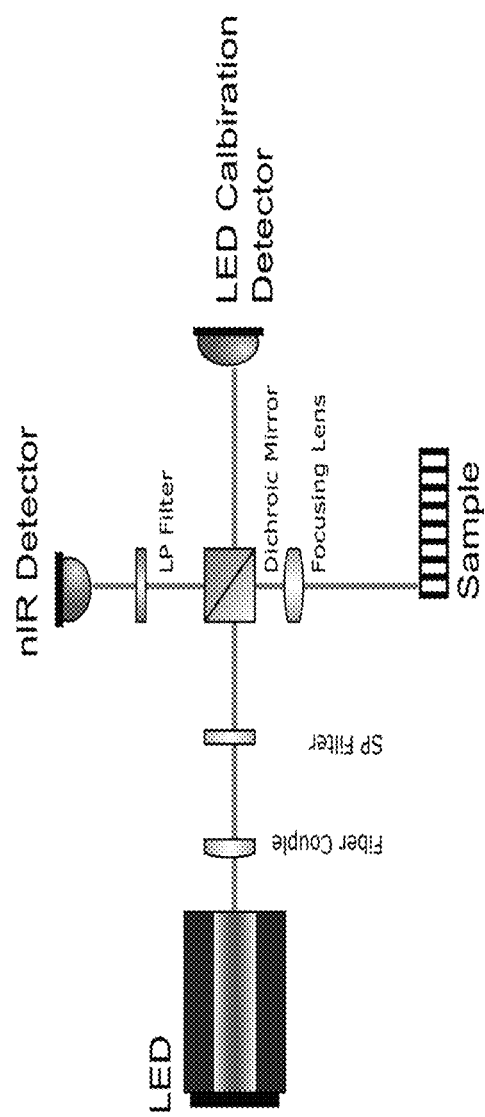

FIG. 12 shows an optical diagram of barcode reader.

Figure 13:
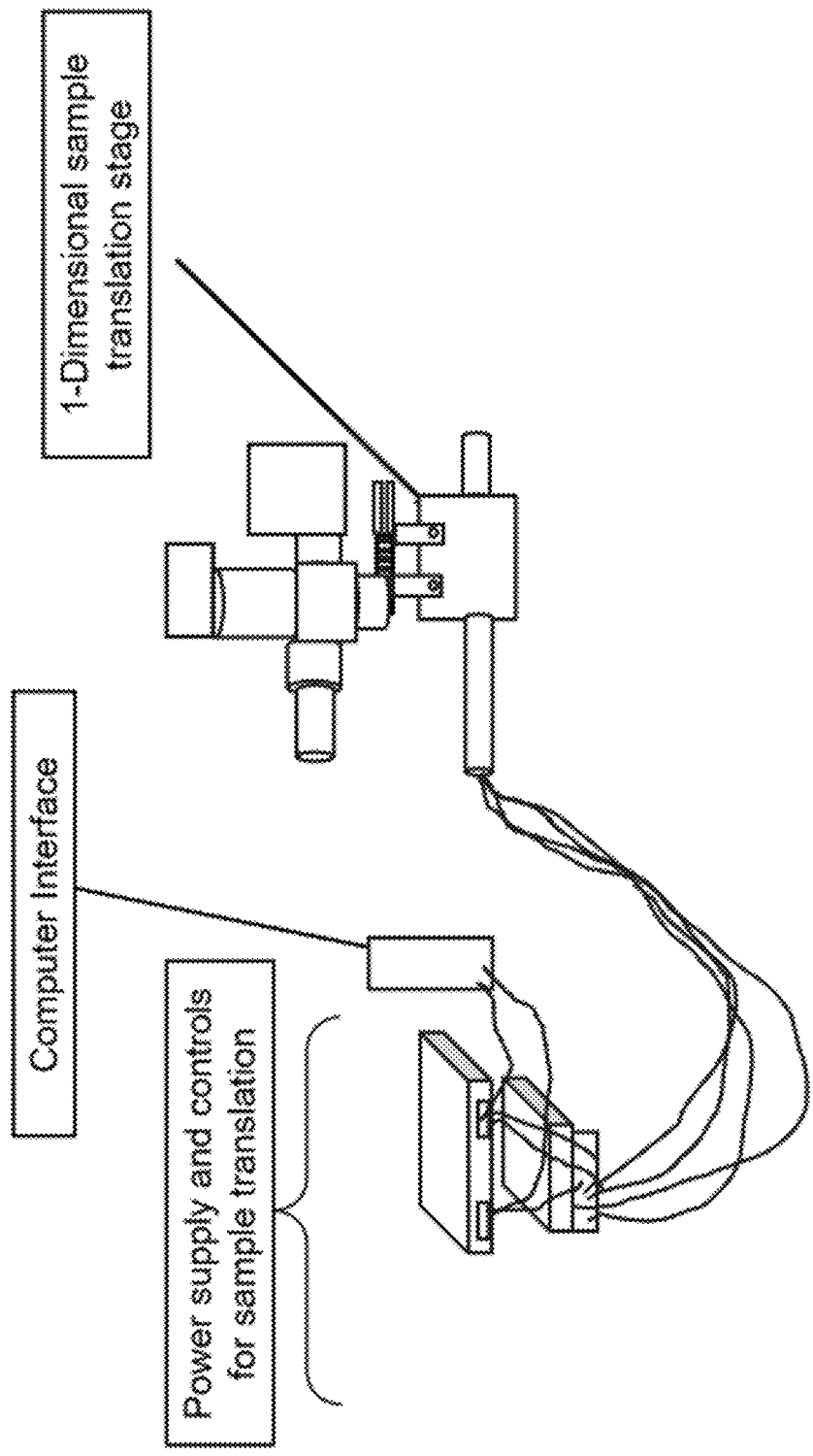

FIG. 13 shows a sensor barcode reader, including power supply and controls for sample translation, a computer interface, and a dimensional sample translation stage.

Figure 14:
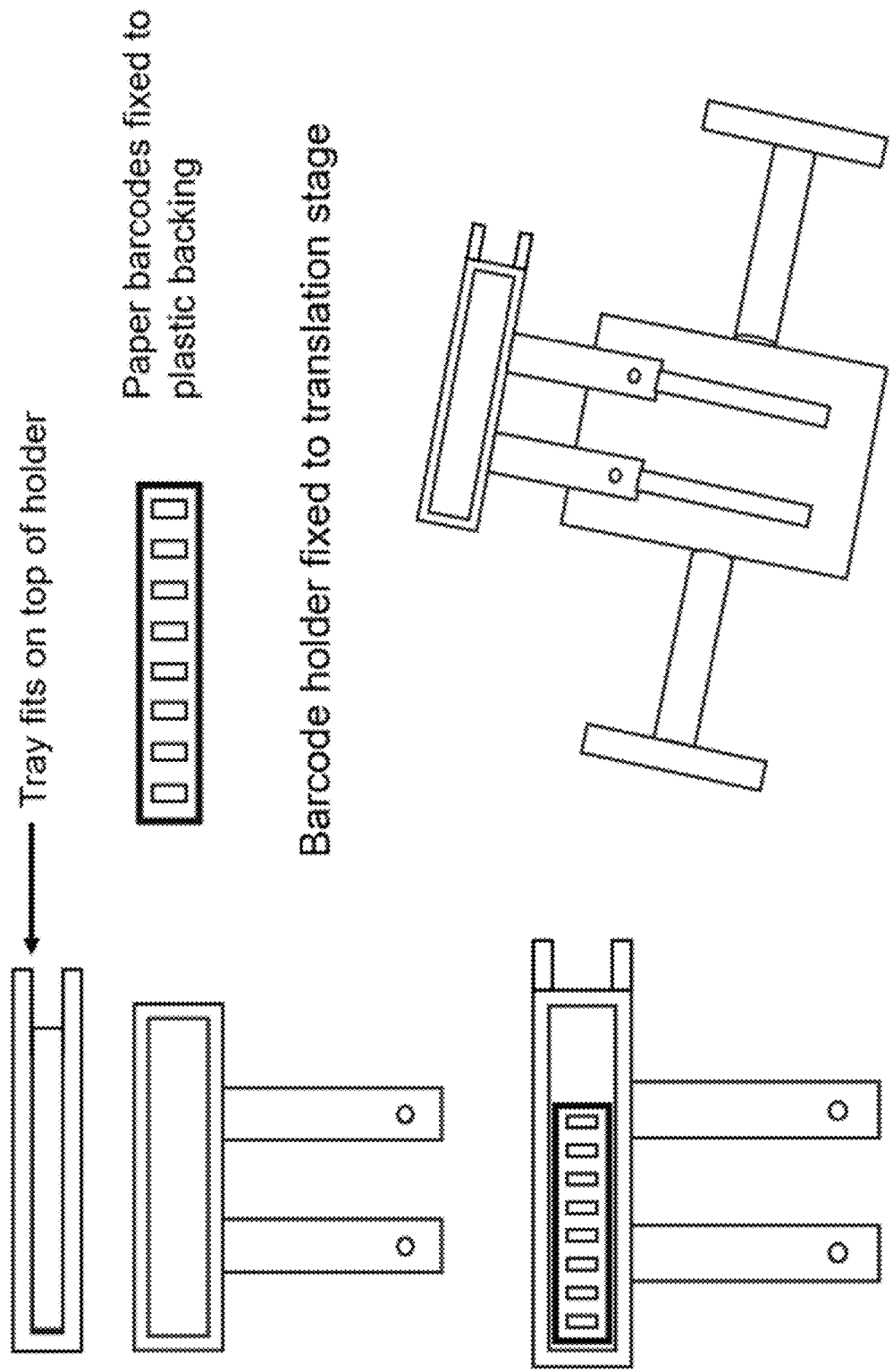

FIG. 14 shows a 3D printed barcode holder. A tray fits on top of holder. A paper barcodes can be fixed to a plastic backing. The barcode holder can be fixed to a translation stage.

Figure 15:
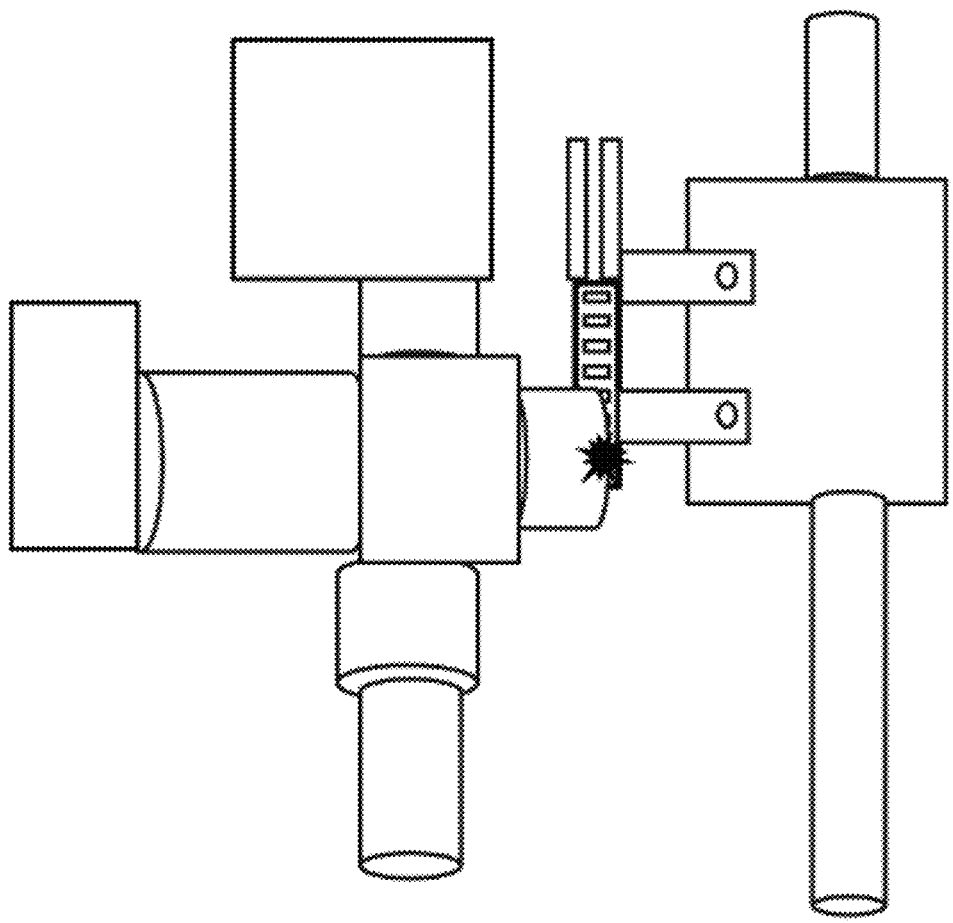

FIG. 15 shows an example of an ongoing scan.

Figure 16:
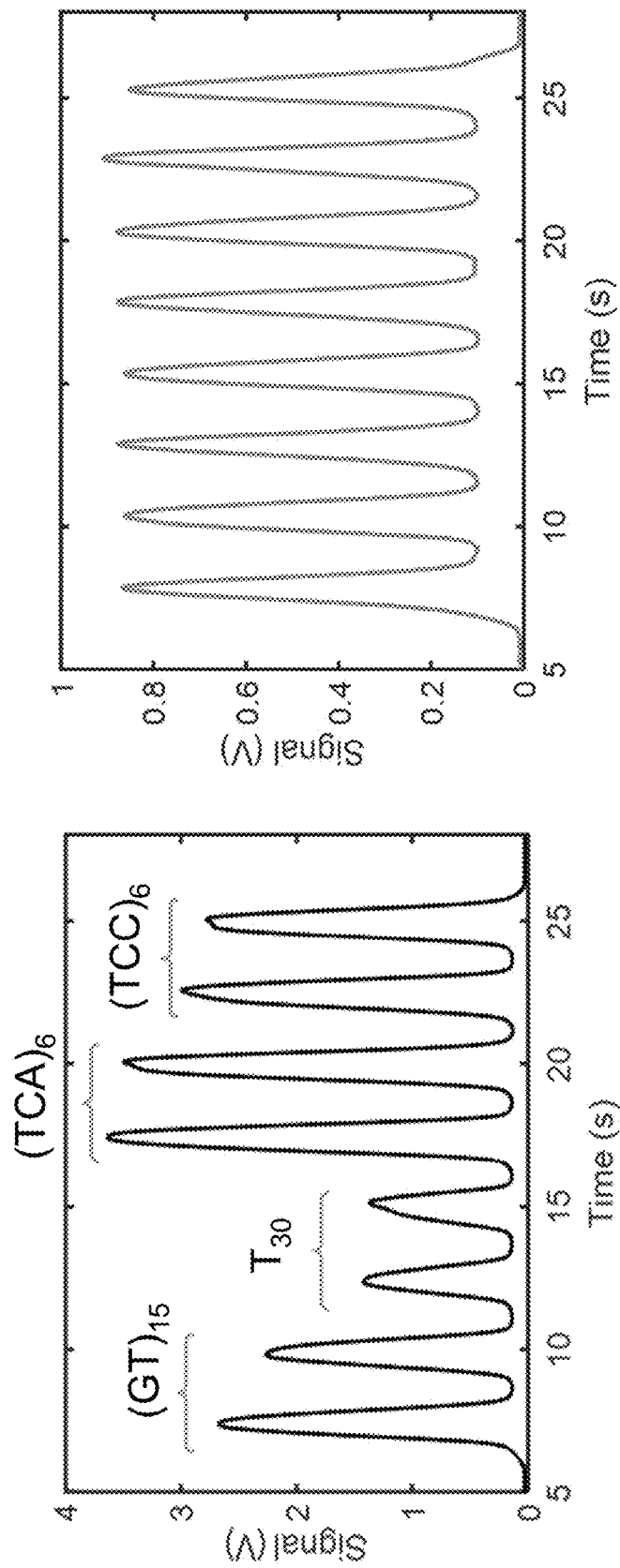

FIG. 16 shows an example of a barcode measurement. A barcode can be made with single-stranded DNA (ssDNA)-wrapped SWNTs. The output shows a blank (no sensors) and with sensors.

Figure 17:
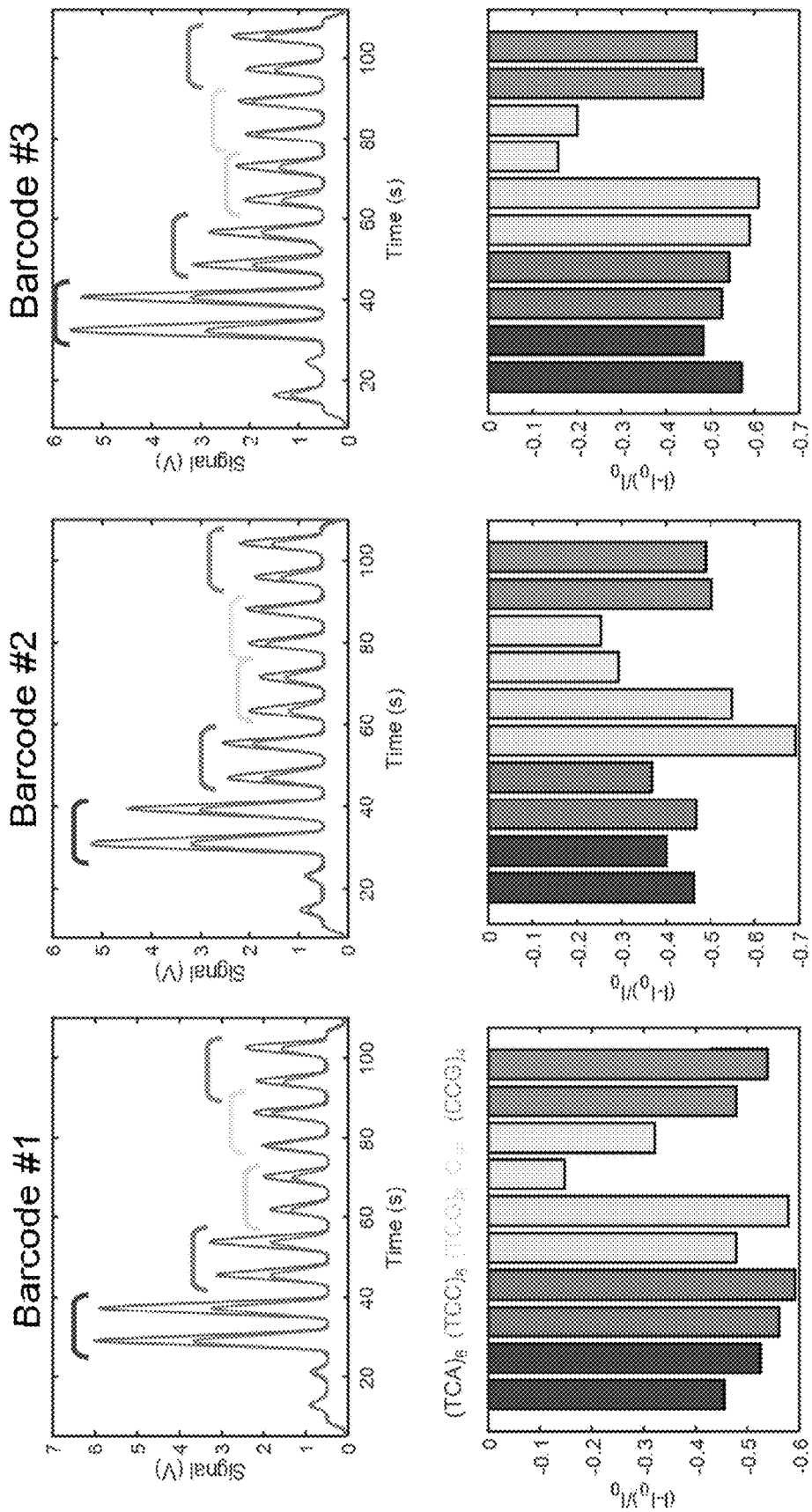

FIG. 17 shows an example of sensor barcode data in response to exposure to copper ion. Sensors are measured in duplicate on each barcode.

Figure 18:
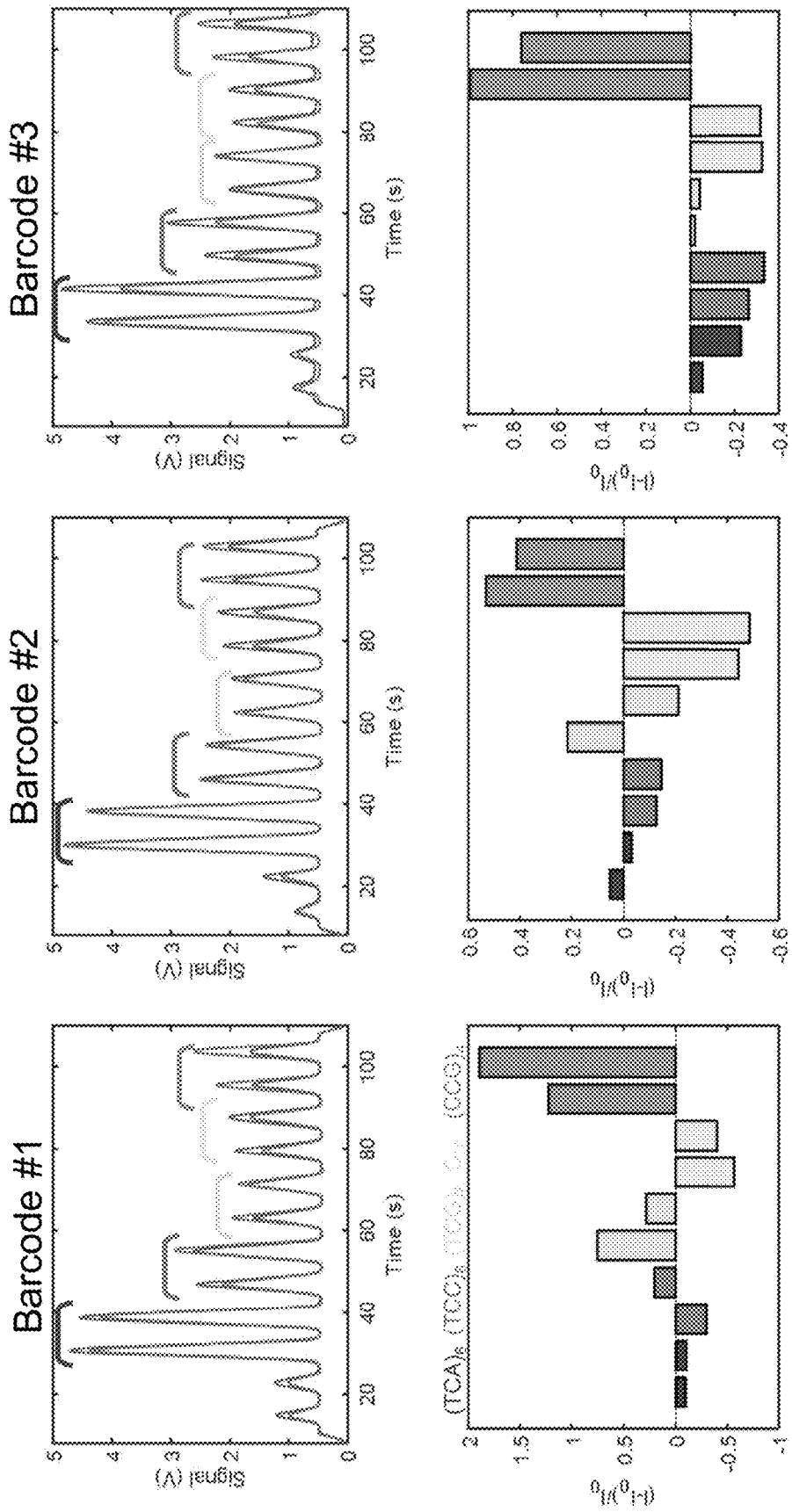

FIG. 18 shows an example sensor barcode data in response to exposure to mercury ion. Sensors are measured in duplicate on each barcode.

FIG. 19 shows metal ion response data measured from sensor barcodes.

Figure 20:
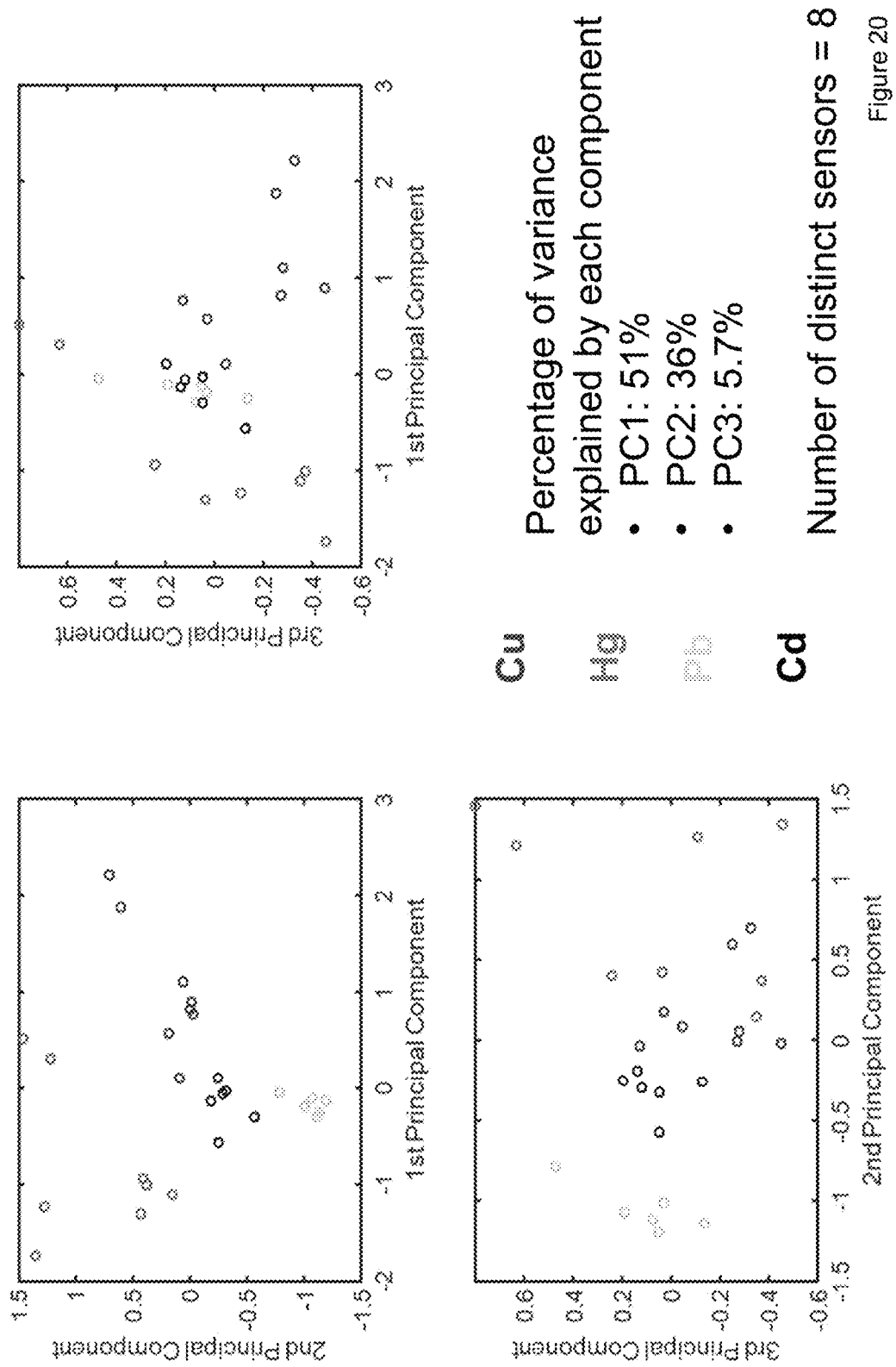

FIG. 20 shows principal component analysis of sensor data for Cu, Hg, Pb and Cd ions. The percentage of variance can be explained by each component using a number of distinct sensors, in this case, eight.

Figure 21:
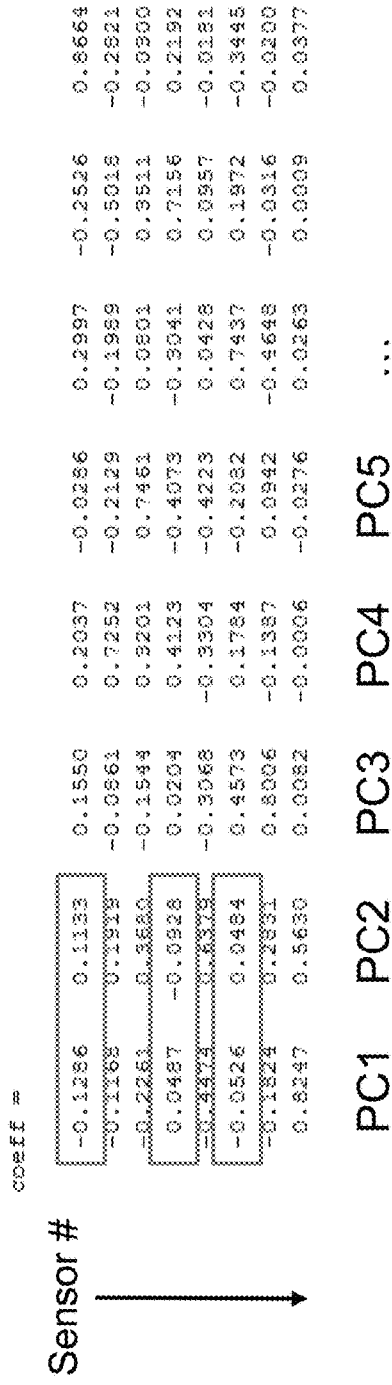

FIG. 21 shows the ability to identify sensors which contribute to principal components Sensors #1, #4 and #6 contribute minimally to the first two principal components which account for 87% of the variance in the data. Additional data can be obtained by removing the sensor data and re-running the PCA analysis.

Figure 22:
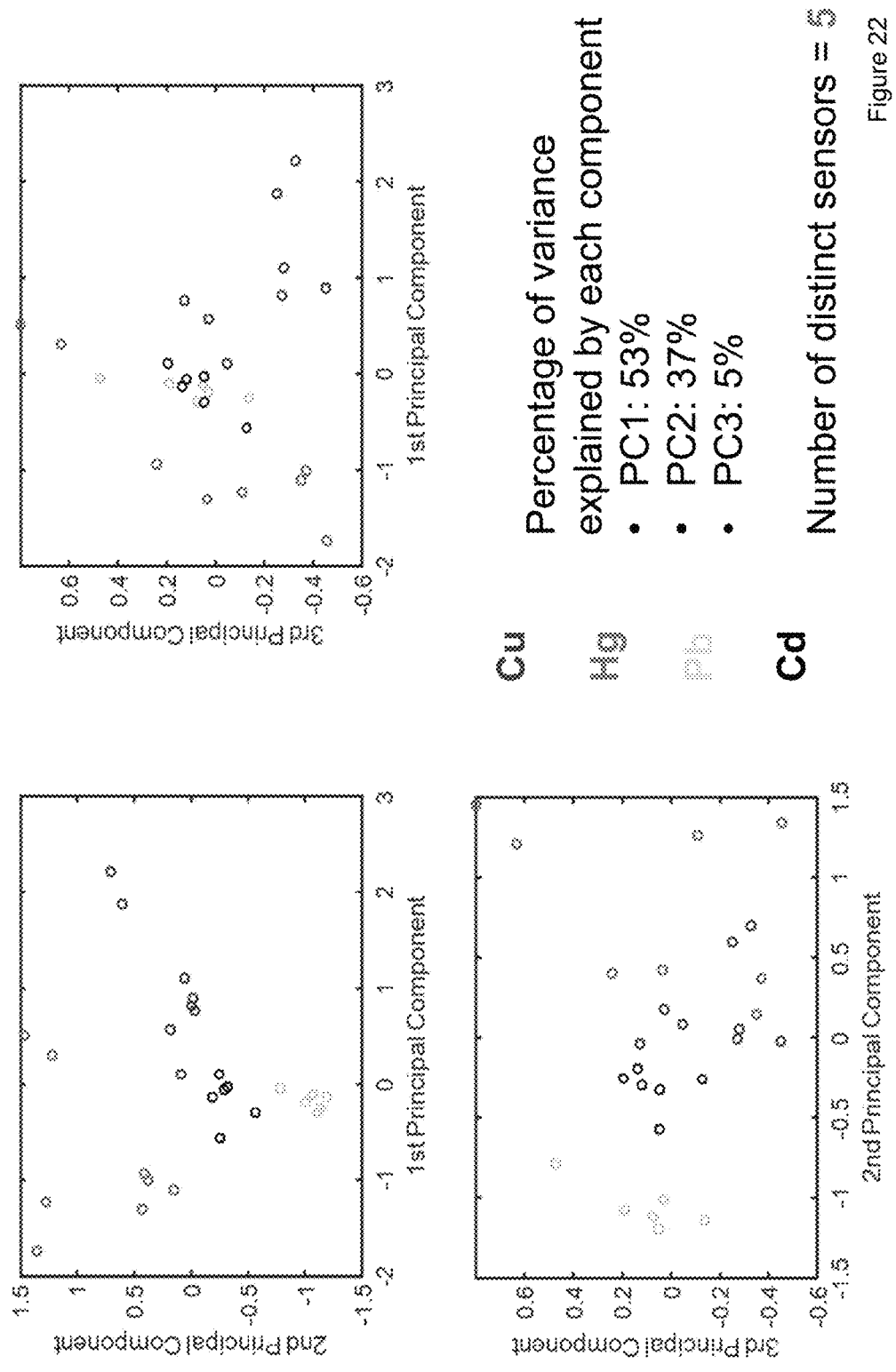

FIG. 22 shows principal component analysis of sensor data with optimized sensor choice for Cu, Hg, Pb, and Cd ions. Relevant data include percentage of variance explained by each component.

Figure 23:
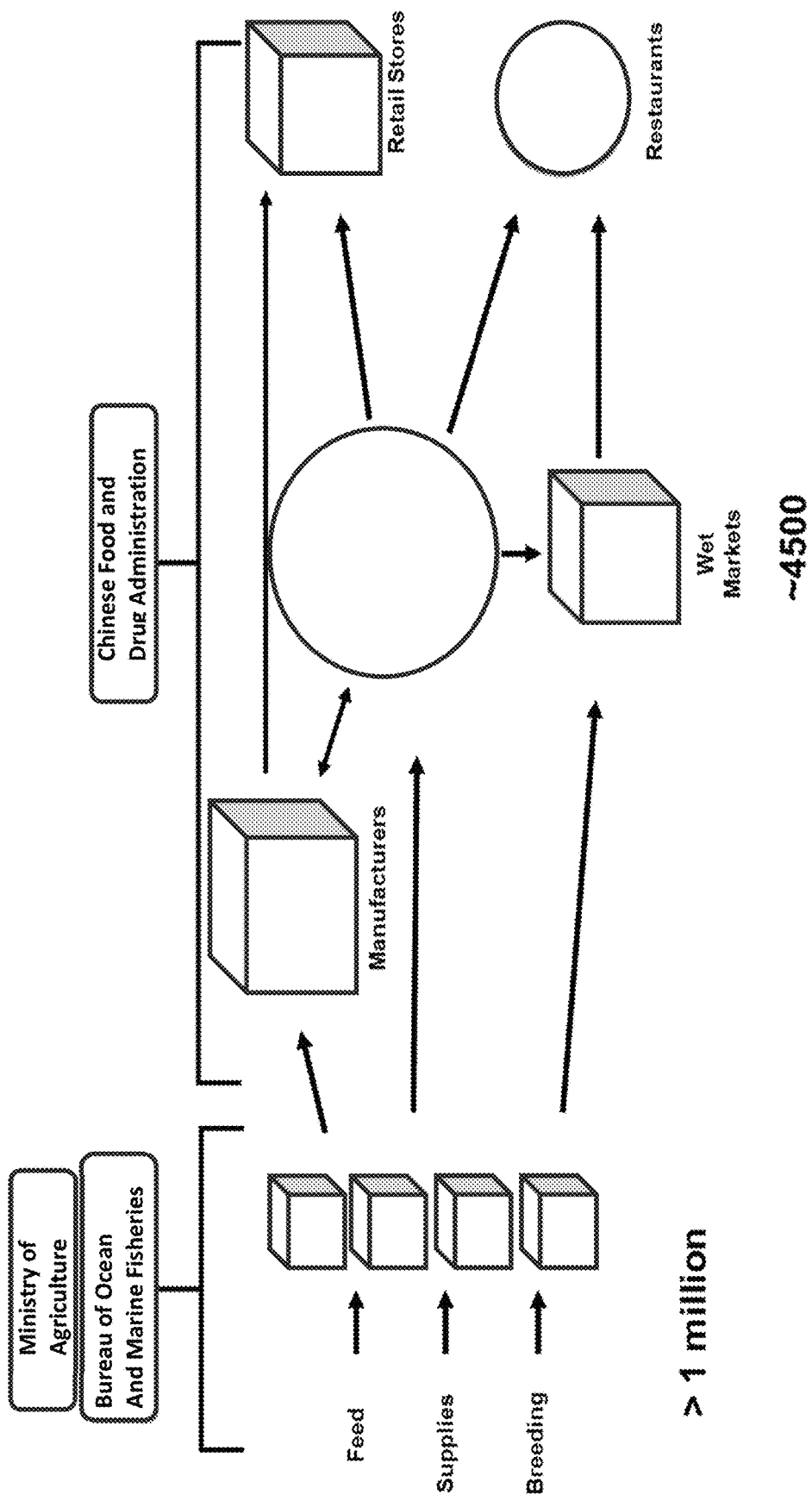

FIG. 23 depicts that sensors of this type can be developed for food/water contaminant detection, for example, in the food supply chain.

Figure 24:
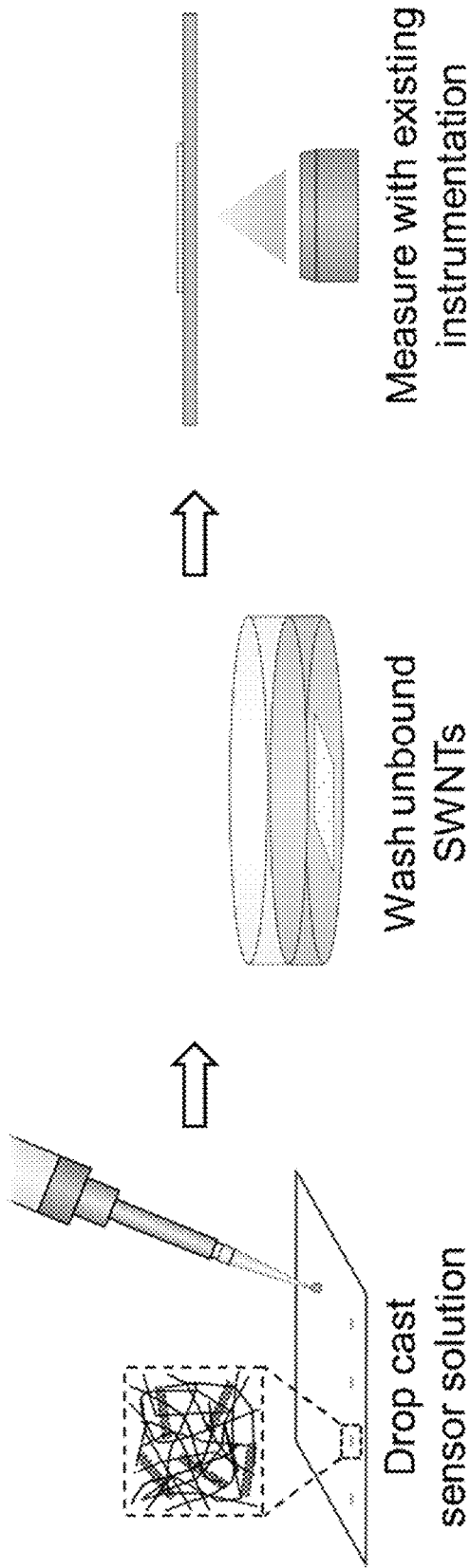
Figure 25:
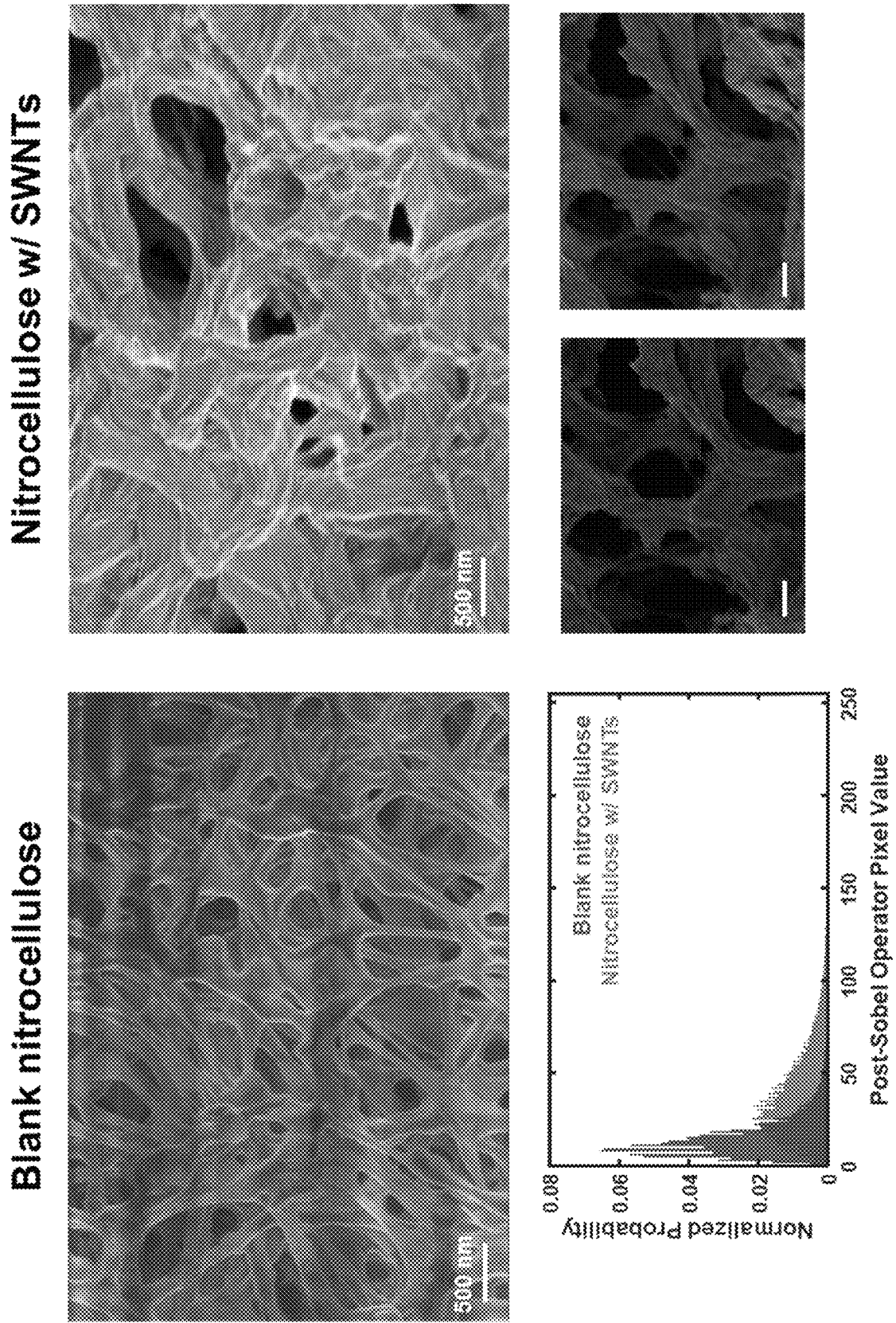

FIG. 24 shows immobilizing SWNT sensors onto porous paper substrates using an immobilization procedure of drop casting a sensor solution, washing unbound SWNTs, and measuring with existing instrumentation FIG. 25 shows SEM images of immobilized SWNTs on blank nitrocellulose and nitrocellulose w/SWNTs.

Figure 26:
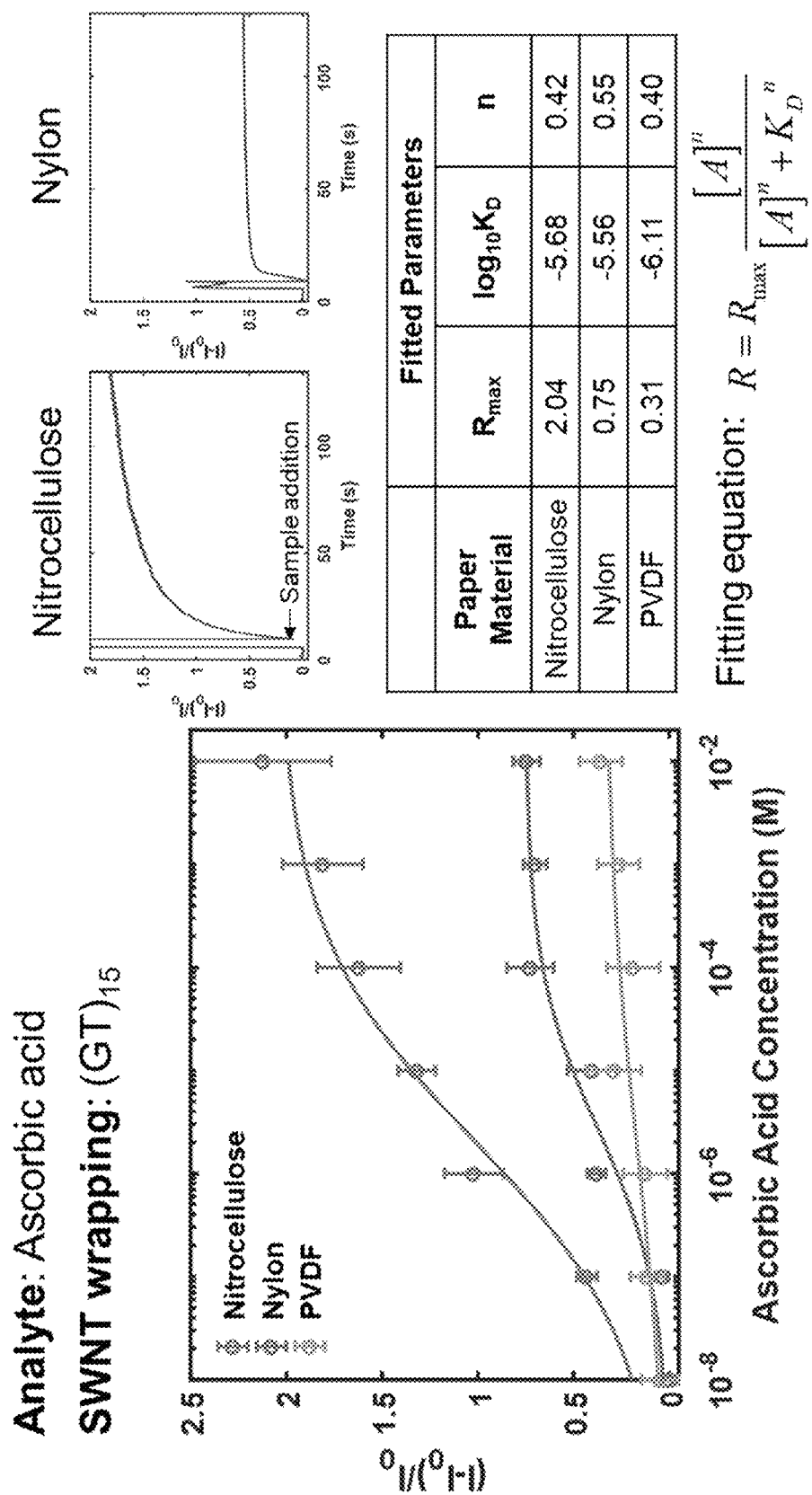

FIG. 26 shows the influence of paper material on DNA-SWNT response to ascorbic acid with a SWNT wrapping of $(GT)_{15}$.

FIG. 27 shows an approach extending beyond aqueous solutions bu performing a CoPhMoRe screen in oil. In this case, the paper material was nitrocellulose, solvent was canola oil, and the samples were menadione (Vitamin K3), retinyl acetate (Vitamin A), (β-carotene (Vitamin A precursor) and α-tocopherol (Vitamin E).

Figure 28:
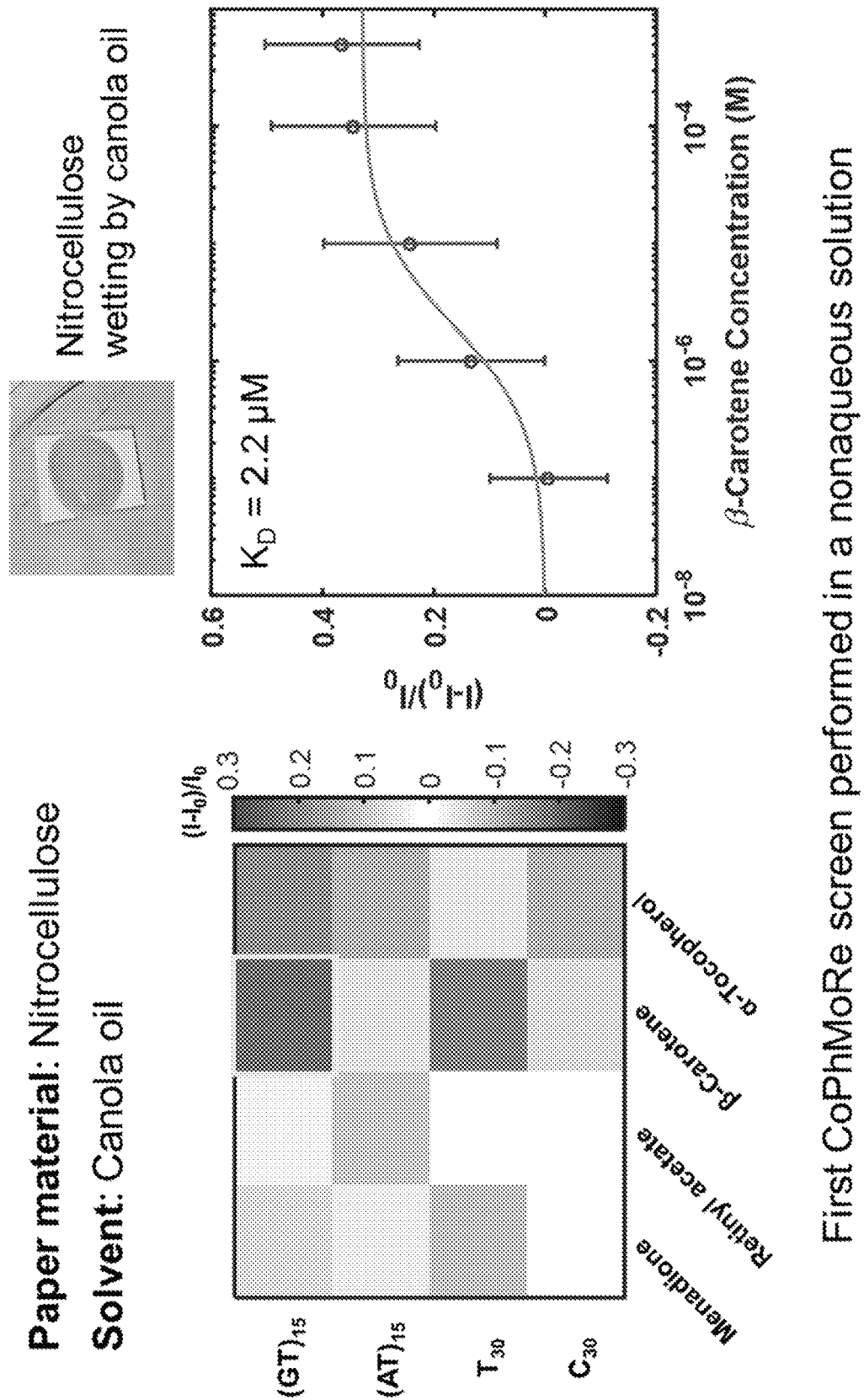

FIG. 28 shows results of the first CoPhMoRe screen performed in a nonaqueous solution, in which paper material was nitrocellulose, solvent was canola oil and the nitrocellulose was wetted by canola oil.

FIG. 3I shows a barcode pattern printed onto nitrocellulose and paper fixed to adhesive plastic backing. The figure also shows the barcode holder and translation stage controls.

Figure 32:
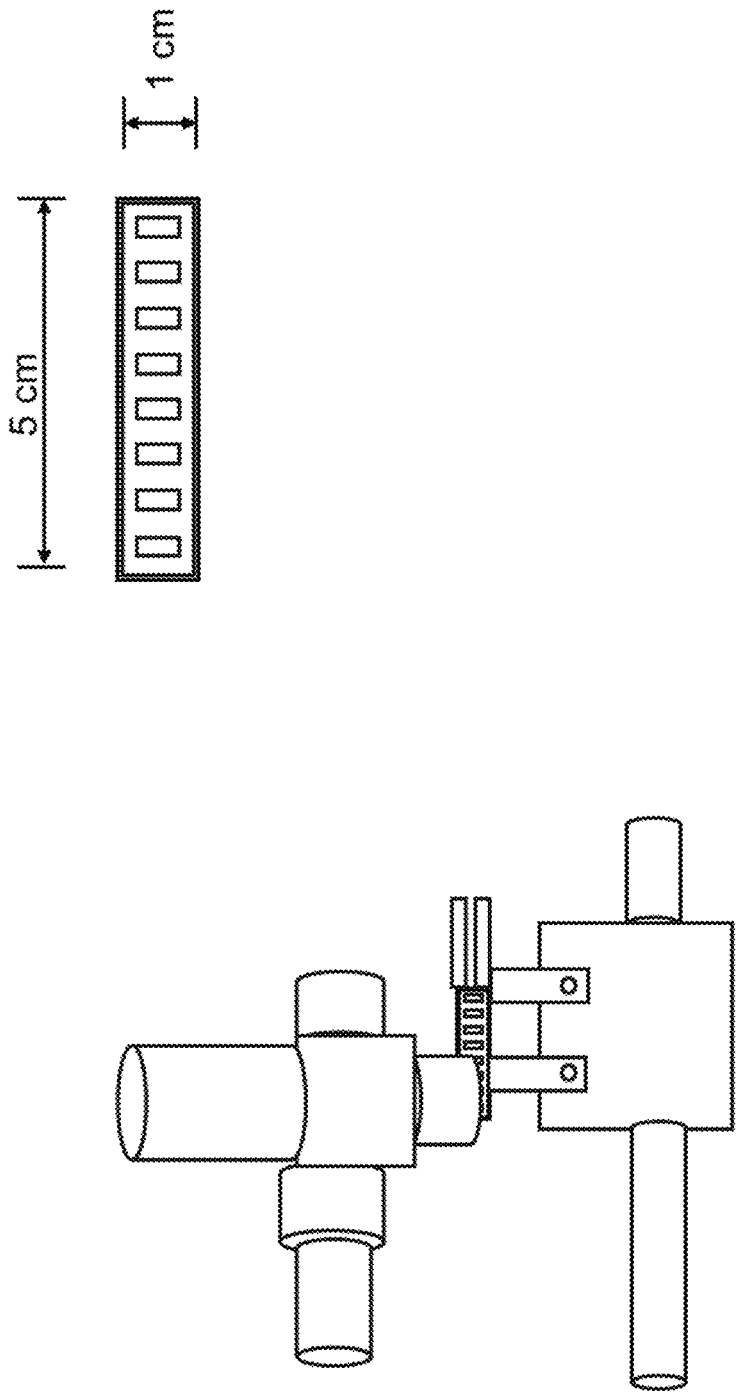

FIG. 32 shows an application of sensor patterning: 1-D sensor "barcode" for rapid multiplexing, in which barcode pattern was printed onto nitrocellulose and paper fixed to adhesive plastic backing. It was shown that it is possible to correlate peak time with barcode position for rapid multiplexing.

Figure 33:
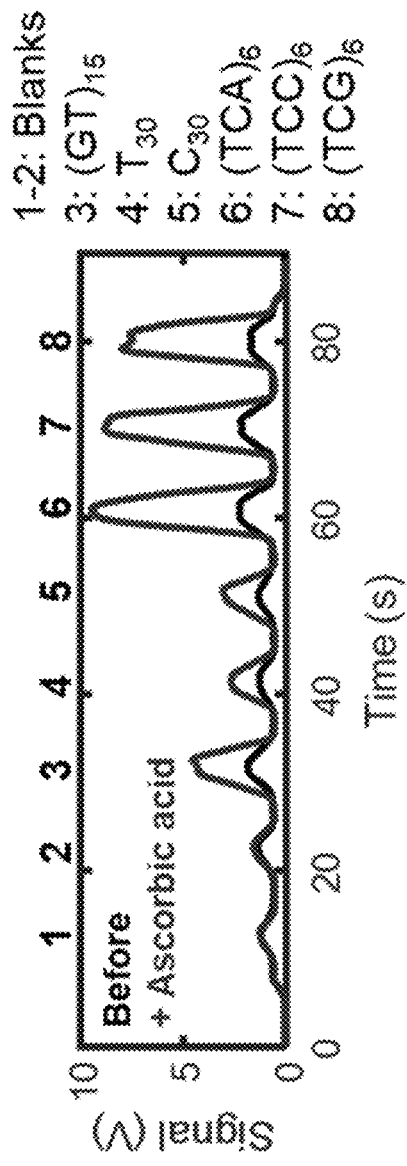

FIG. 33 shows a demonstration of multiplexing using sensor barcodes for metal ion discrimination. Eight different ssDNA wrappings were screened against four metal ions using the barcode form factor Barcodes dipped in metal solutions. The ssDNA sequences were $(TCA)_6$, $(TCC)_6$, $(TCG)_6$, $(GT)_{15}$, $C_{30}$, $(CCG)_4$, $(TAT)_4$, $(ATTT)_3$. The metal ions were Cu, Hg, Pb, Cd (all at 100 µM). In this example, each example barcode had five sensors. Principle component analysis (PCA) was performed on the most optimal five wrappings.

Figure 34:
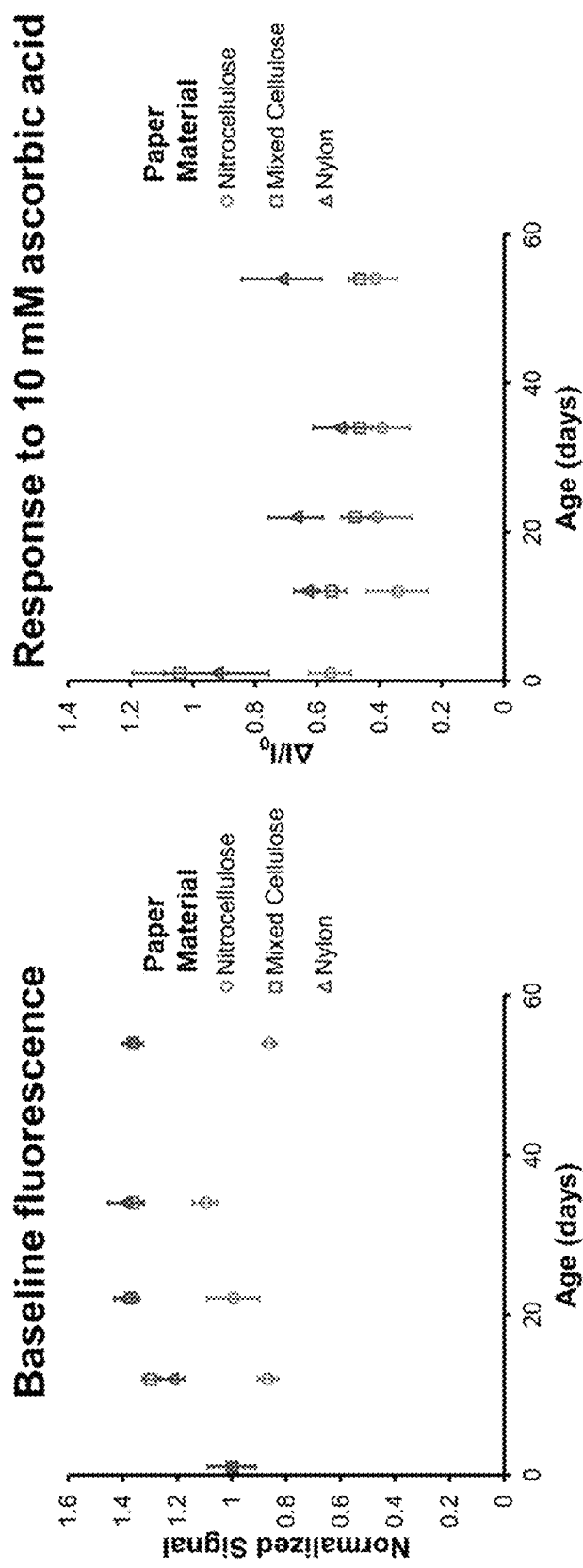

FIG. 34 shows sensor responsivity maintained for nearly 60 days. In this experiment, the SWNT wrapping was $(ACCA)_7$, samples were blocked with 5% milk and stored in airtight bags, and data was obtained to show baseline fluorescence and response to 10 mM ascorbic acid. Sensor samples were transported internationally and performed identically to samples stored at the site of fabrication and yielded substantially similar results, showing robust stability to a variety of temperature, pressure, and humidity conditions.

FIG. 35 shows conclusions of the performance of the sensors. The SWNT sensors can be immobilized on various paper substrates and remain responsive after immobilization. The SWNT sensors can be patterned onto paper for enhanced functionality. Prolonged oxygen exposure can irreversibly reduce SWNT fluorescence.

Other embodiments are within the scope of the following claims.

What is claimed is:

1. A sensor for detecting one or more analytes, comprising:
a porous planar substrate having a plurality of regions, and a second region including a second photoluminescent structure different from a first photoluminescent nanostructure; and
at least one photoluminescent nanostructure on or embedded within the sensor porous planar substrate in a first region, and a second photoluminescent structure different from the first photoluminescent nanostructure in a second region.

2. The sensor of claim 1, further comprising an analyte-binding compound associated with the photoluminescent nanostructure.

3. The sensor of claim 2, wherein the photoluminescent nanostructure includes a polymer.

4. The sensor of claim 3, wherein the polymer includes a polypeptide, a polynucleotide or a polysaccharide.

5. The sensor of claim 3, wherein the polymer is a polynucleotide.

6. The sensor of claim 1, wherein the plurality of regions includes at least three distinct regions.

7. The sensor of claim 1, wherein the porous planar substrate is a paper, nitrocellulose, or nylon, or combinations thereof.

8. A method of making a sensor for detecting one or more analytes, comprising:
depositing a photoluminescent nanostructure on or within a porous planar substrate to form a plurality of regions, a first photoluminescent nanostructure on or embedded within the sensor porous planar substrate in a first region, and a second photoluminescent structure different from the first photoluminescent nanostructure in a second region.

9. The method of claim 8, further comprising patterning the porous planar substrate to include a plurality of regions, at least one region receiving the photoluminescent nanostructure.

10. The method of claim 8, wherein depositing includes placing a liquid including the photoluminescent nanostructure on the porous planar substrate.

11. A method of detecting an analyte, comprising:
contacting a sensor including a photoluminescent nanostructure on or embedded within the porous planar substrate having a plurality of regions, a first photoluminescent nanostructure on or embedded within the sensor porous planar substrate in a first region, and a second photoluminescent structure different from the first photoluminescent nanostructure in a second region; with a sample; and
detecting an output from the sample to determine the presence of the analyte.

12. The method of claim 11, wherein detecting includes measuring the output at two or more regions of the porous planar substrate.

13. The method of claim 11, further comprising moving the porous planar substrate relative to a detector.

14. The method of claim 13, wherein moving the porous planar substrate relative to a detector occurs at a controlled rate.

15. A system for detecting an analyte, comprising:
a platform including a sample holder;
a detector including a directed at the platform; and
a translation stage including an axis of motion orthogonal to the contacting a sensor including a photoluminescent nanostructure on or embedded within the porous planar substrate with a sample, the porous planar substrate having a plurality of regions, at least one photoluminescent nanostructure on or embedded within the sensor porous planar substrate in a first region, and a second photoluminescent structure different from the first photoluminescent nanostructure in a second region.

16. The system of claim 15, wherein translation stage moves the platform at a controlled rate.

17. The system of claim 15, further comprising an photoexcitation device.

* * * * *